(12) United States Patent
Heikkilä

(10) Patent No.: US 9,463,131 B2
(45) Date of Patent: Oct. 11, 2016

(54) SPINAL THERAPY APPARATUS

(76) Inventor: Markku Heikkilä, Piikkiö (FI)

( * ) Notice: Subject to any disclaimer, the term of this patent is extended or adjusted under 35 U.S.C. 154(b) by 1163 days.

(21) Appl. No.: 12/085,364

(22) PCT Filed: Nov. 27, 2006

(86) PCT No.: PCT/FI2006/000391
§ 371 (c)(1),
(2), (4) Date: May 22, 2008

(87) PCT Pub. No.: WO2007/060282
PCT Pub. Date: May 31, 2007

(65) Prior Publication Data
US 2009/0270914 A1    Oct. 29, 2009

(30) Foreign Application Priority Data
Nov. 25, 2005  (FI) ...................................... 20051207

(51) Int. Cl.
*A61H 1/02*     (2006.01)
*A61H 1/00*     (2006.01)
*A61F 5/30*     (2006.01)

(52) U.S. Cl.
CPC ............ *A61H 1/0292* (2013.01); *A61H 1/006* (2013.01); *A61H 1/008* (2013.01); *A61H 1/02* (2013.01); *A61H 1/0296* (2013.01); *A61F 5/30* (2013.01); *A61H 2201/1261* (2013.01); *A61H 2205/081* (2013.01)

(58) Field of Classification Search
CPC .......... A61H 1/00; A61H 1/008; A61H 1/02; A61H 1/0218; A61H 1/0292; A61H 1/0296; A61H 2205/08; A61H 2205/081; A61H 1/006; A47C 20/207; A47C 16/005; A61G 7/07; A61G 13/1225

USPC .......... 601/23, 24, 49, 134, 135; 602/32–36; 606/240, 237; 128/845, 112.1, 116.1, 128/121.1; 5/630, 632, 633, 636, 640, 643
See application file for complete search history.

(56) References Cited

U.S. PATENT DOCUMENTS

| | | | | |
|---|---|---|---|---|
| 1,833,426 A * | 11/1931 | Knudson | ...................... | 606/240 |
| 2,159,654 A * | 5/1939 | Catlin | ........................ | 606/240 |
| 3,831,592 A * | 8/1974 | Lancellotti | ................ | 601/135 |
| 6,036,719 A * | 3/2000 | Meilus | ...................... | 606/204 |
| 6,110,194 A * | 8/2000 | Saber | ........................ | 606/240 |
| 6,810,542 B1 * | 11/2004 | Mitchell | ........................ | 5/630 |
| 2004/0078055 A1 * | 4/2004 | Kusumi | .................... | 606/240 |
| 2005/0203445 A1 * | 9/2005 | Tsai | .......................... | 601/15 |

* cited by examiner

*Primary Examiner* — Alireza Nia
*Assistant Examiner* — Keri J Nelson
(74) *Attorney, Agent, or Firm* — Kubovcik & Kubovcik

(57) ABSTRACT

A spinal therapy apparatus including at least one gripping member whose direction deviates from the transverse direction relative to the spinal column, so that the angle between the gripping member and the midline of the spinal column is less than 90°. A gripping member unit includes preferably two gripping members the angle between the ridges of the gripping members being less than 180°. There is a gap or groove between the gripping members. The gripping member unit also includes a support part, the support part being padded, preferably including two parts and in an inclined position relative to the floor. There is a groove between the gripping member and the support part. The spinal therapy apparatus may also incorporate at least one support handle, which the user can use to move the required part of the spinal column to the ridges of the gripping members.

18 Claims, 34 Drawing Sheets

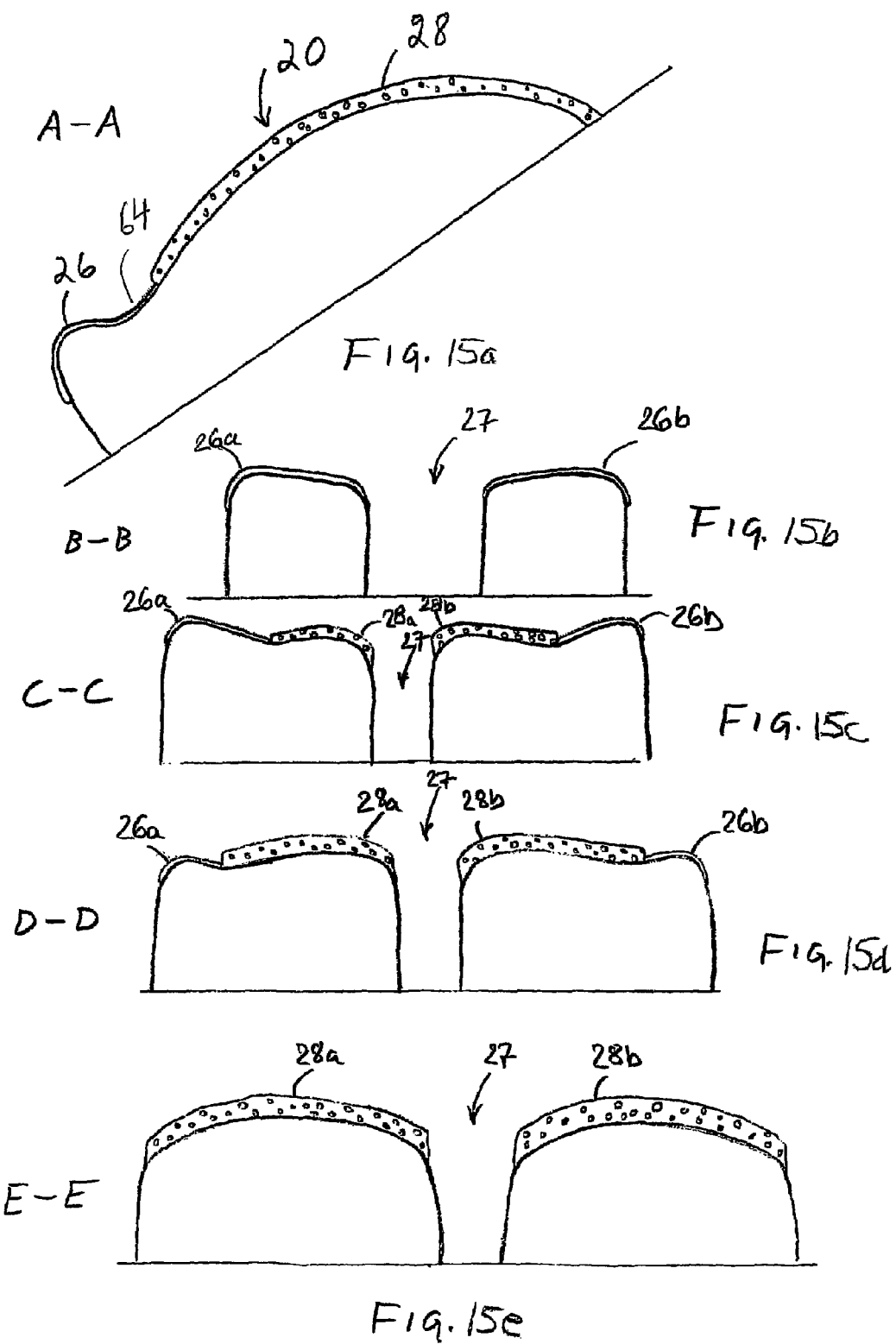

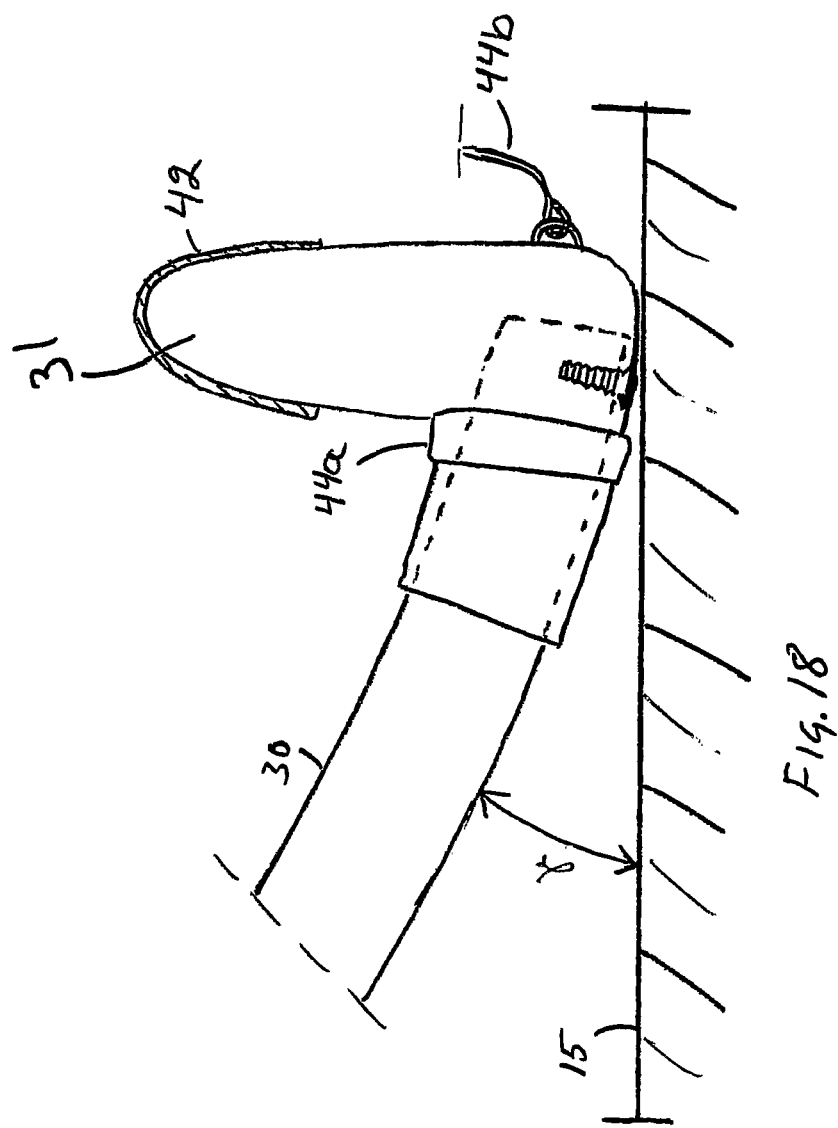

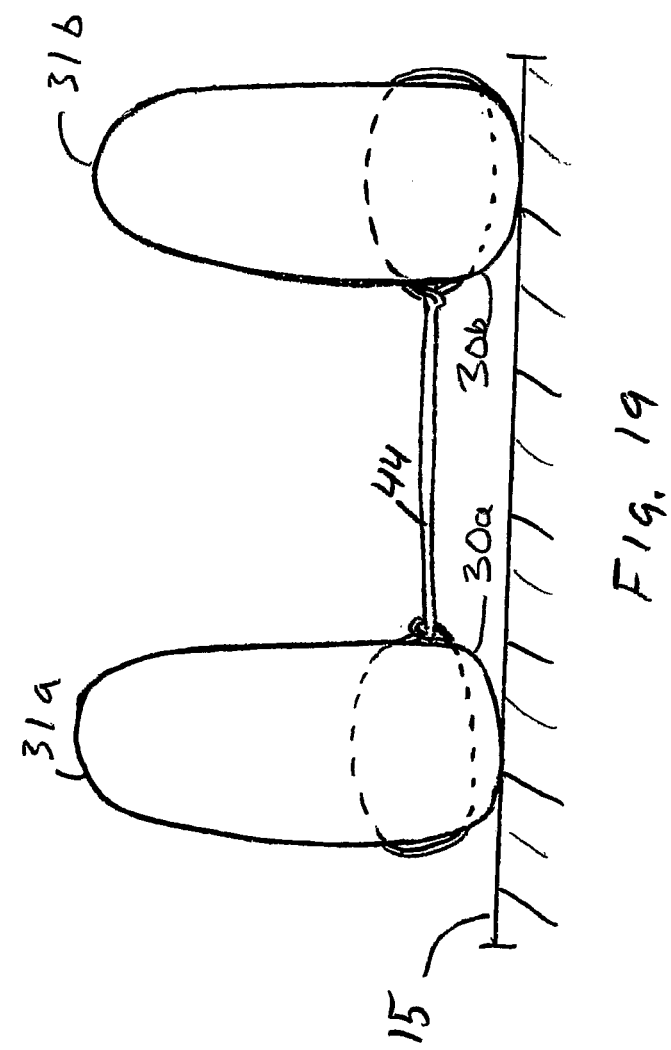

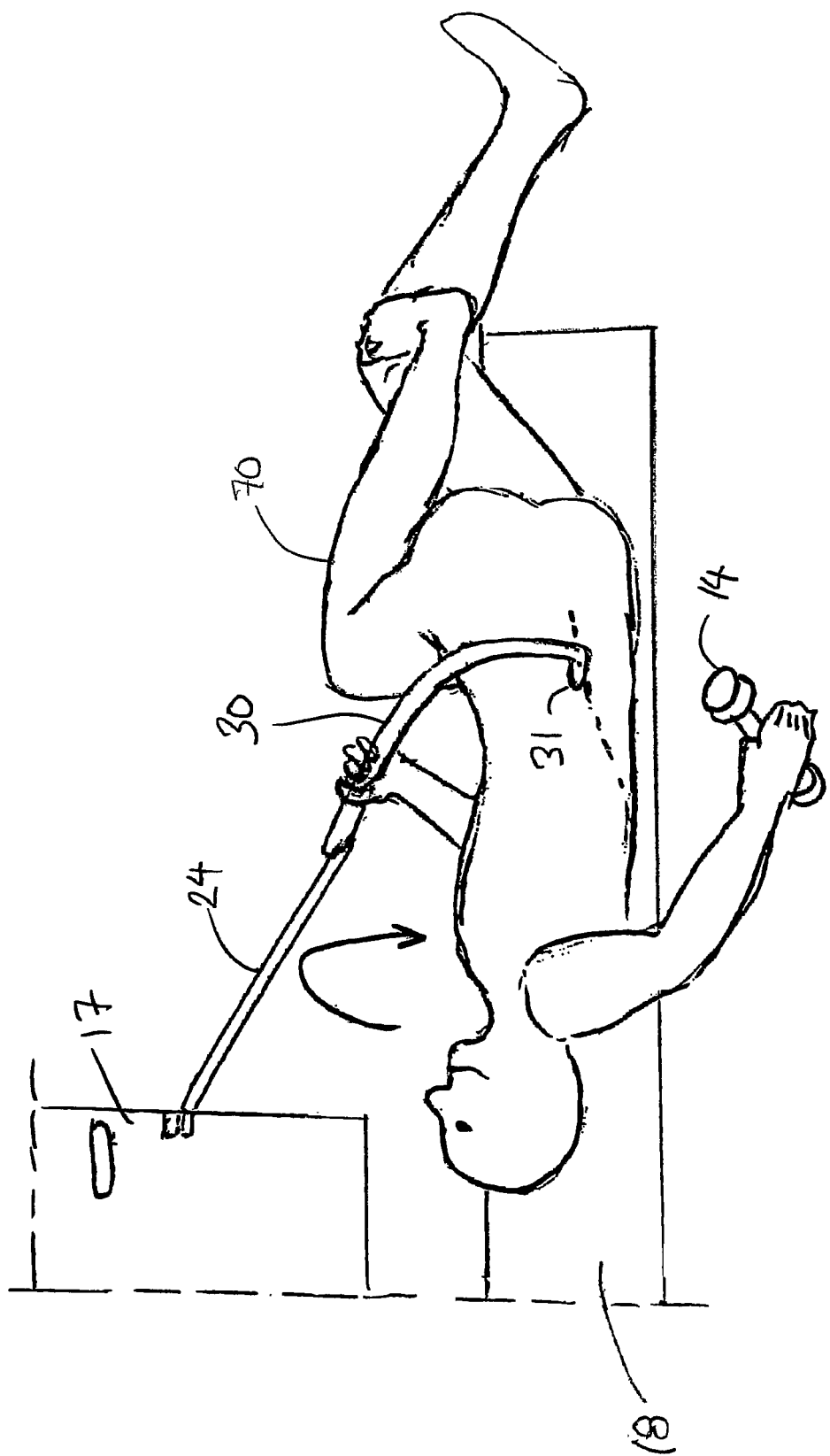

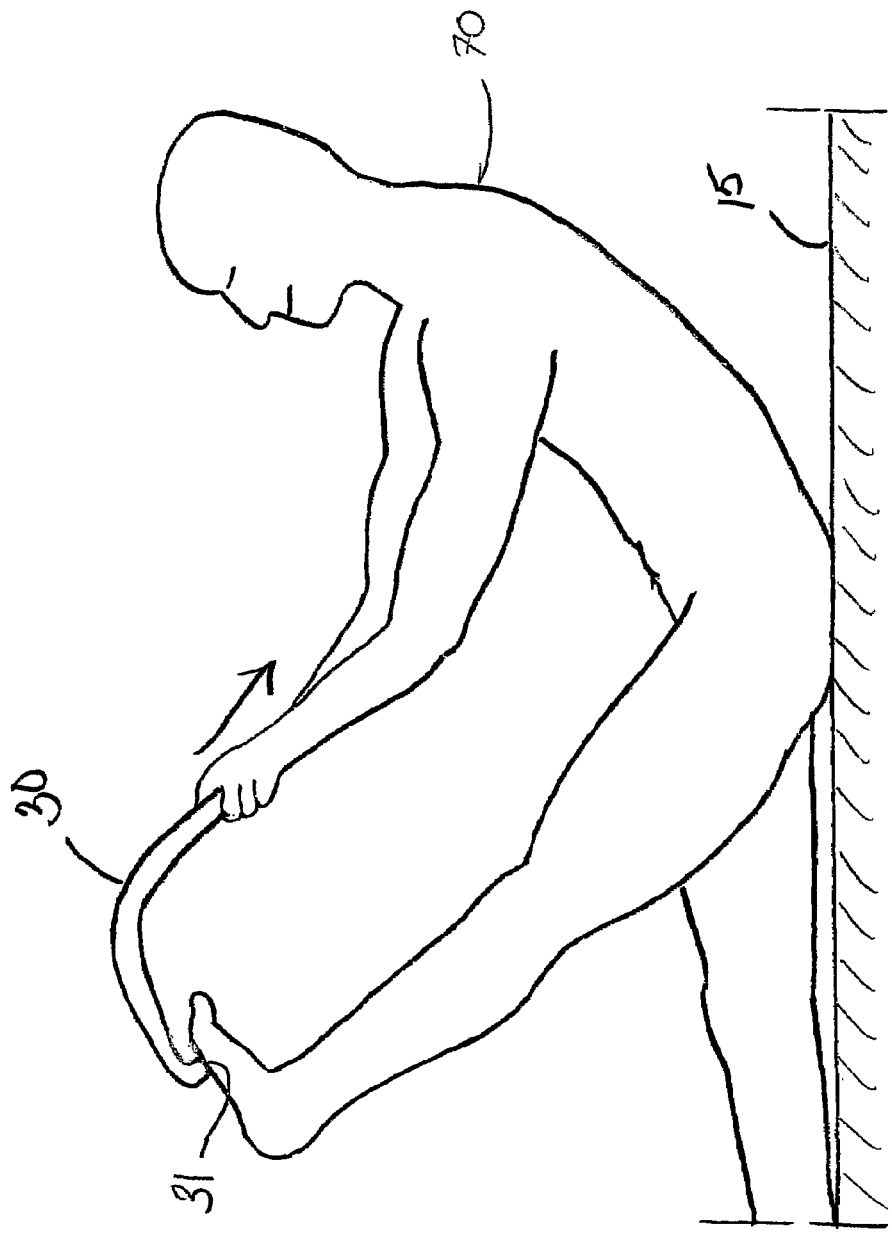

SPINAL THERAPY APPARATUS

This application is a 371 of international application PCT/FI2006/000391 filed Nov. 27, 2006, which claims priority based on Finnish patent application No. 20051207 filed Nov. 25, 2005, which is incorporated herein by reference.

OBJECT OF THE INVENTION

The object of the invention being presented is a spinal therapy apparatus having at least one member placed against the back of a person using the apparatus for treating the spinal vertebrae.

PRIOR ART

It has been observed that an increasing proportion of the various illnesses affecting the human population will be spinal ailments. Approximately 9% of disability cases are currently caused by spinal conditions, and all in all as many as four in five persons suffer from some sort of back pain during their lives. Pain in the back is typically caused by locking of the zygapophyseal joints, poor mobility in the spinal joints, problems affecting the intervertebral discs or tension in the spinal muscles.

Alleviation of back pain is sought with serial treatments by therapists, but these are relatively expensive. Visiting the therapist may also cause many people difficulties. For these reasons there have been attempts to create a spinal therapy apparatus that would make it possible for people to treat themselves.

Solutions for a spinal therapy apparatus have been presented in the patent publications U.S. Pat. No. 5,676,626, U.S. Pat. No. 5,925,003, U.S. Pat. No. 6,041,457 and U.S. Pat. No. 6,110,194. However, the precision of treatment, ease of use and effectiveness of the known apparatuses for spinal therapy have remained insufficient.

PURPOSE OF THE INVENTION

The purpose of this invention is to present a new spinal therapy apparatus, which does not have the problems of the known apparatuses for spinal therapy. It is another object of the present invention to create a spinal therapy apparatus that better takes into account the anatomy of the spinal vertebrae, and thus achieves a substantially improved precision in the treatment compared with the known apparatuses. It is further another object of the present invention to create an apparatus that will help to alleviate various ailments of the back and will allow the sufferer him- or herself to locate and mobilise the painful area in the back at home or when travelling, i.e. will make possible recovery of the mobility of spinal vertebrae.

CHARACTERISTICS OF THE INVENTION

The spinal therapy apparatus according to the invention is characterised in that
  the spinal therapy apparatus includes a gripping member, which gripping member may be adjusted so as to be placed between the spinal vertebrae of the person using the apparatus, a single vertebra or a vertebral interspace at a time,
  the gripping member is comprised of a ridge, a rounded edge, a line formed by two or more protrusions or a similar elongated member which, between two spinal vertebrae, can be disposed so as to apply pressure to the required vertebra, and
  the elongated gripping member can be fitted into a vertebral interspace so that one end of the gripping member is close to the midline of the spinal column, at a distance from the spinal column, and the opposite end of the gripping member is directed away from the midline of the spinal column, obliquely to the side, non-parallel to the transverse direction of the spinal column and in part towards the shoulder of the user in such a way that the angle between the elongated gripping member and the midline of the spinal column is less than 90°.

A spinal therapy apparatus according to the invention takes into account the anatomy of the vertebrae in a more beneficial way than known apparatuses, because the contact of the gripping member, which is in an oblique position, is applied to processes in the extremities of a single vertebra. As a result of this, the apparatus gives maximum efficiency of support of the vertebra for the flexional and tensional forces in various directions applied when treating the spinal column.

It is essential in a spinal therapy apparatus according to the invention that, in the gripping member unit, a ridge forms the gripping member, which may be accurately set to any required vertebral interspace. Thereafter, such a gripping member makes it possible, by means of friction, to accurately grip a single vertebra and treat that particular vertebra. A spinal therapy apparatus according to the invention can also be used for preventive purposes and for helping recovery after heavy physical activity.

EMBODIMENTS OF THE INVENTION

A preferred embodiment of the spinal therapy apparatus according to the invention is characterised in that the angle $\alpha$ between the gripping member of the spinal therapy apparatus and the midline of the spinal column is 15°-80° or, most preferably, 40°-60°.

Another preferred embodiment of the spinal therapy apparatus according to the invention is characterised in that the elongated gripping member can be adjusted in a vertebral interspace so that the end of the gripping member that is closer to the midline of the spinal column applies pressure to the processus articularis inferior of the vertebra or the inferior portion of the lamina and the opposite end of the gripping member applies pressure to the processus transversus or the processus costarius of the same vertebra.

A third preferred embodiment of the spinal therapy apparatus according to the invention is characterised in that
  the spinal therapy apparatus includes one or several gripping members that form a continuous ridge, a ridge comprised of one or several protrusions or a similar arrangement, and that
  the ridge or a similar arrangement can be disposed between spinal vertebrae on one side of the spinal column or on both sides of the midline of the spinal column of the person using the apparatus.

The gripping members are either pressed against the spinal column of the person using the apparatus or the person can press him/herself against the members.

A fourth preferred embodiment of the spinal therapy apparatus according to the invention is characterised in that
  the spinal therapy apparatus includes a gripping member unit with two gripping members, the gripping members are ridges, rounded edges, lines of two or more protrusions or similar elongated members which can be disposed to apply pressure to the required vertebra on both sides of the midline of the spinal column simultaneously, and that one end of both gripping members is close to the midline of the spinal column, at a distance from the spinal column, and the opposite ends of the gripping members are directed away from the midline of the spinal column, obliquely to the side, non-parallel to the transverse direction of the spinal column and in part towards the shoulder of the user, so that the angle between the gripping members is less than 180°.

A fifth preferred embodiment of the spinal therapy apparatus according to the invention is characterised in that the angle 2α between the elongated gripping members on both sides of the midline of the spinal column is 30°-160° or, most preferably, 80°-120°.

A sixth preferred embodiment of the spinal therapy apparatus according to the invention is characterised in that the spinal therapy apparatus includes a frame, at least one gripping member unit to be pressed against the spinal column and at least one handle, on which the person using the apparatus support him/herself, in that the gripping member unit is comprised of a support part, which the person using the spinal therapy apparatus can use as a support, which support part is padded or hard and most preferably comprised of two parts and most preferably in an oblique position relative to the floor level, two ridges of the gripping members, between which there is a depression or a gap, and which ridges of the gripping members are located below the support part, and at least one support handle, a pair of support handles, rope or a similar arrangement, which the user of the spinal therapy apparatus can grip, support him/herself on, lean on or hang from in order to place the required part of the spinal column at the point where the ridges of the gripping members of the gripping member unit are positioned.

A seventh preferred embodiment of the spinal therapy apparatus according to the invention is characterised in that the gripping member unit of the spinal therapy apparatus is a friction pad located above the floor, at a sitting height most preferably approximately 20-70 cm from the floor and at standing height most preferably approximately 50-100 cm from the floor, at least a part of which friction pad is tilted forward, and the tips of the ridges in the gripping member unit are at the same level or become lower towards the opposite ridge and correspondingly rise towards to outer edge of the gripping member unit, and in that there is a groove or gap between the ridges and the support part of the gripping member unit.

Thus the ridges of the gripping member unit, i.e. the gripping members, can be placed between two spinal vertebrae, whereby the ridges of the gripping members grip by means of friction one vertebra at a time, immobilising it. The groove between the ridges of the gripping members and the support part in the gripping member unit is intended for a skin fold and to make it easier to position the ridge on the painful area of the back.

GLOSSARY

The following Latin terminology relating to the spinal column is used in the text below:

traction=lengthwise stretching of the spinal column
extension=stretching of the spinal column backwards
flexion=stretching of the spinal column forward
rotation=rotational movement of the spinal column
vertebrae=the small bones forming the backbone
lamina=the posterior part of the vertebral arch
processus transversus=transverse process (thoracic spine)
processus costarius=costal process (lumbar spine)
costae=ribs
ilium=iliac bone
processus mamillaris=mamillary process
processus spinosus=spinous process (central)

In order to obtain optimal results from the therapy, it is necessary to be able locate the painful area to a specific vertebra and to stretch the spinal column accordingly. Compared to known apparatuses for spinal therapy, the pressure can be exerted more beneficially parallel to the arch and processes of a single vertebra because the angle of the friction-forming ridges of the gripping members relative to the midline of the spinal column is less than 90°. When the ridges of gripping members of the gripping member unit are on both sides of the midline of the spinal column, the angle between the ridges is less than 180°. This also increases the force in traction, extension and rotation without impairing comfort of use. Furthermore, all these directions of motion can easily be achieved simultaneously if so required, by means of hand supports and control by feet.

Because the user of the spinal therapy apparatus can, by means of the support handles, adjust each portion of his/her spinal column accurately to the ridges of the gripping members of the gripping member unit he/she can perform the following single movements or various, simultaneous combinations of them at the required intensity and in the required direction for each vertebra specifically: traction, extension, rotation and flexion.

The motive power for these movements is the Earth's gravity, i.e. the spinal therapy apparatus user's own weight, in combination with the steering movements carried out by the user. Among these, traction, i.e. lengthwise stretching of the spinal column, is extremely important because it lowers the internal pressure in a spinal segment. This also stretches soft tissues such as muscles, ligaments and annular fibres in intervertebral discs. Decompression in an intervertebral disc reduces the susceptibility to prolapse or protrusion. At the same time, the nerve root openings expand in the area being treated, which provides more space for the nerve roots. It is essential in this respect that the therapy can be efficiently applied to a single vertebral interspace at a time. By treating all vertebral interspaces in such a way it is possible to provide improved mobility, metabolism, blood circulation and alleviation of pain in the entire spinal column. Mobilisation of the iliac bones is also possible with the spinal therapy apparatus. It is further possible to use additional weights with the spinal therapy apparatus.

Embodiments of the spinal therapy apparatus according to the invention may vary. Therefore, the angle of inclination of the spinal therapy apparatus or of the gripping member unit relative to the floor, i.e. reclining angle β, is 30°-70°, most preferably 40°-50°. The spinal therapy apparatus may also include two gripping member units, a lower gripping member unit and an upper gripping member unit, and most preferably, the inclination and distance of the gripping member units relative to each other can be adjusted.

According to one embodiment of the invention, the spinal therapy apparatus includes at least one pair of support handles, for example one support handle on each side of the apparatus, which support handles are located in front of or behind the gripping member unit, above it, at the gripping member unit or below the gripping member unit, and the support handle is a curved rod directed upwards, a handle directed to the side or forward, a rope handle or an armrest.

The spinal therapy apparatus may include an adjustable fastening member, such as a strap or hooks to fasten the spinal therapy apparatus to a chair, stand, rack or other similar object, the object being most preferably located against a wall to prevent it sliding backwards. The apparatus may also include a floor rest with adjustable length and inclination, which floor rest, when the spinal therapy apparatus is fastened to a chair or other similar object, keeps the apparatus in place and prevents the chair or other object from tilting forward and simultaneously functions as a strap tightener. The floor rest is most preferably padded, in which case it also provides a backrest for treating the neck.

According to one embodiment of the invention, the spinal therapy apparatus includes two additional supports resting on the floor, which supports can be turned and tilted to a suitable position according to the height of the seat and detached for transport. Both additional supports have been provided with an additional handle that can be adjusted in the vertical direction or, alternatively, with several fixed steps at various heights.

The spinal therapy apparatus may also include a shaft portion; said shaft portion being an upwards-directed, padded, curved rod; said shaft portion being attached to the frame of the spinal therapy apparatus so as to turn around it; and said portion part having a rounded end portion at the end of its support handle, which end portion forms a gripping head. The shaft portion can be detached so that the gripping head can be used separately for applying pressure to or massaging or mobilising the back, and in particular for rotation.

The spinal therapy apparatus includes, as an additional fitting, a rubber mat to be fastened to the floor rest or chair legs, which rubber mat prevents the chair from sliding backwards and functions as a mat for lying on when using the gripping head. The spinal therapy apparatus may also include a stand with support legs or a support rack or the spinal therapy apparatus may be fastened to a fixed structure such as a wall or floor, in which case the apparatus includes an additional handle or rope supported on its frame or another structure, floor, ceiling or wall.

The number and shape of the gripping members may vary, but it is essential that they are adapted to the anatomy of the spinal column so that they can be readily pressed to the required area of the spinal column, against any vertebra. The gripping member may also be comprised of a single ridge, but it may also be comprised of two or more protrusions, which in this case are substantially located in a single line.

It is essential that the gripping member comprised of the ridges or protrusions forms an angle of less than 90° relative to the lengthwise axis of the spinal column. When there are gripping members on both sides of the midline of the spinal column they comprise a gripping member unit. In such a case, the gripping members comprise an angle of less than 180° relative to each other. There is also an interspace, such as a gap or a depression, between the gripping members on both sides of the midline of the spinal column, against the processus spinosus at the midline of the spinal column.

It is essential for a gripping member unit according to the invention that the length and angle of the gripping members on both sides of the midline of the spinal column relative to the lengthwise axis of the spinal column are such that they are suitable for gripping a single vertebra at a time. In such a case, the ridges touch the following points on both sides of the vertebra in the area of the chest (thorax): the processus tranversus and the processus articularis inferior or the processus tranversus and the inferior portion of the lamina. In the lumbar area (lumbus), the processus costarius corresponds to the processus tranversus. To make it possible to press the gripping members against the required vertebra, the angle between the gripping members on both sides of the midline of the spinal column must according to the invention be less than 180°.

A gripping member according to the invention may be comprised of a shaped object which includes the ridge or protrusions. The ridge comprising the gripping member may in such a case be comprised of an edge or corner of a relatively hard object, which edge or corner may also be padded and/or rounded to improve comfort of use. The ridge may be smooth or it may be made roughened or provided with protuberances or otherwise shaped or coated to increase friction.

In the simplest form, however, the gripping member may, for example, be a rod or plate shaped so that the edge comprising the ridge that penetrates between the vertebrae is straight, concave or slightly convex. The surface next to the ridge, resting on the spinal column, may also be straight, concave or convex.

A gripping member according to the invention may be positioned in several different ways in the spinal therapy apparatus, allowing the user, depending on the apparatus, to sit, stand, lie or hang or be stretched on a vertical, horizontal or an inclined surface. When the gripping member is attached to a chair in an inclined position the user leans against the pair of gripping members in the gripping member unit so that the required vertebrae can be treated one at a time.

When the gripping member is used in an inclined position, for example attached to a chair, it is preferable that there is a support part above the ridges comprising the gripping members, such as a support pad, against which the user leans. When the support part is above the ridges, the support part supports the vertebrae and preliminarily stretches the soft tissues.

The support part may be hard or padded, and convex, flat or concave in form, and it may be comprised of two parts so that the halves are separated by a gap. It is also preferable to separate the support parts entirely or in part from the ridges by a gap or a groove, in particular in the central and frontal areas of the ridges. At the outer edge, the ridge may equally well continue, forming a support part, as it turns upwards. The outer edge of the ridge may most preferably be higher than the frontal, i.e. inner edge.

A spinal therapy apparatus comprising a chair may include a foldable or telescopic neck rest. According to one embodiment of the invention, the armrests of the chair are provided with protrusions on their underside and have additional handles at their ends. The front legs of the chair may be detachable so that they can be used as separate gripping heads. Height adjustment of the chair may be realised by providing the shaft portion of the gripping head, at the intersection of the straight and the curved portion, with holes or notches on the side of the outer curve. The notches improve the stability when the shaft portion is gripped by hand, as seen below in FIG. 22.

Height adjustment of the armrests of the chair may also be electrically powered. In such a case the apparatus may also be used by a person in a weak condition, because it is not necessary to change the point at which the armrests are gripped. The operating switch of the adjustment system may, for example, be in the handle, and the height is raised by a gear rack, by means of a hydraulic system or by a wire rope and pulley, for example.

The gripping member may also be attached to a special spinal therapy apparatus resembling a chair, in which case the gripping member is incorporated in the backrest, and the seat is comprised of a exercise ball filled with air, the elasticity of which ball can be adjusted by regulating the pressure of air within it. The ball receives the pelvis at the point when the user lowers him-/herself during the treatment. The ball also functions as a "bearing" between the body and the floor. The ball moves when the user lowers him-/herself in the spinal therapy apparatus and stops when arrested by strings attached to the front legs of the spinal therapy apparatus. When the ball is released by lifting the pelvis, it is restored to its initial position pulled, for example, by a rubber band.

A shaft portion may also be attached to the gripping member. Such an arrangement allows several different embodiments of the spinal therapy apparatus for various uses. A single gripping member may be used by a single shaft portion. According to one embodiment of the invention, a gripping member at the end of a shaft portion may be turned so as to form a gripping head. The user leans against the gripping member or lies supine on the gripping member on a base, such as the floor. In such a case, the user may change the position of the gripping member located between the back and the floor and in this way control the gripping member so as to apply the treatment to any area of the spinal column. Various heads may be fastened to the end of the shaft, for example by quick-release systems or screws. The heads may be hard or slightly padded.

Two gripping members may both be provided with shafts and combined in various ways. The gripping members may be attached to each other by means of a flexible band, such as a ribbon, or by a hinge pin, thus providing an efficient gripping member unit with two gripping members.

A gripping member according to the invention can, however, be used in any stretching apparatus or a motorised and/or automated apparatus. Furthermore, the gripping member unit may be a pressing device to be held in the hand, with which a therapist can treat the spinal vertebrae of a person lying prone, from above. In such a case, the ridges of the gripping members are located in a pressing pad, on the opposite side of which there are handles.

According to one preferred embodiment of the invention, the height of a gripping member of the spinal therapy apparatus may be adjusted independently from the adjacent gripping member. Such a solution may, for example, be an arrangement where one of the gripping members is or both of the gripping members are separately hinged at one end. In such a case, either of the ridges can be separately raised or lowered. The motion may be simultaneous with a motion of the support part or a part of it. In this way, either of the ridges of the gripping members may be tilted relative to the ridge of the adjacent gripping member. The adjustment may be mechanised so that the angles of inclination of the ridges in the gripping members may adjusted as required by using a switch in the handle of the spinal therapy apparatus.

EMBODIMENTS

In the following, the invention is described using examples with reference to the appended drawings, wherein

LIST OF FIGURES

FIG. 1 is a perspective view of a spinal therapy apparatus according to the invention attached to a chair.

FIG. 2 is a perspective view of another embodiment of the spinal therapy apparatus.

FIG. 3 is a perspective view of a third embodiment of the spinal therapy apparatus attached to a chair.

FIG. 4 is a perspective view of a fourth embodiment of the spinal therapy apparatus attached to a chair.

FIG. 5 is a perspective view of a fifth embodiment of the spinal therapy apparatus.

FIG. 6 is a schematic side view of a method of using the spinal therapy apparatus in FIG. 5.

FIG. 7 is a schematic side view of another method of using the spinal therapy apparatus in FIG. 5.

FIG. 8 is a perspective view of a sixth embodiment of the spinal therapy apparatus.

FIG. 9 is a side view of a seventh embodiment of the spinal therapy apparatus attached to a chair.

FIG. 10 is a top view of a seventh embodiment of the spinal therapy apparatus.

FIG. 11 is a side view of an eighth embodiment of the spinal therapy apparatus.

FIG. 12 is a perspective view of a ninth embodiment of the spinal therapy apparatus.

FIG. 13 is a side view of a tenth embodiment of the spinal therapy apparatus and of alternative solutions of the embodiment.

FIG. 14 is a perspective view of an embodiment of the gripping member unit of the spinal therapy apparatus.

FIG. 15a is a sectional view of FIG. 14 along the line A-A.

FIG. 15b is a sectional view of FIG. 14 along the line B-B.

FIG. 15c is a sectional view of FIG. 14 along the line C-C.

FIG. 15d is a sectional view of FIG. 14 along the line D-D.

FIG. 15e is a sectional view of FIG. 14 along the line E-E.

FIG. 16a is a top view of another embodiment of the gripping member unit of the spinal therapy apparatus.

FIG. 16b is a sectional view of FIG. 16a along the line A-A.

FIG. 16c is a sectional view of FIG. 16a along the line B-B.

FIG. 17a is a side view of a third embodiment of the gripping member unit of the spinal therapy apparatus and an adjustment piece related to it.

FIG. 17b is a side view of the gripping member unit in FIG. 17a with the adjustment piece installed in its place.

FIG. 17c is a bottom view of the gripping member unit in FIG. 17a.

FIG. 18 is a detail of an embodiment of the gripping head shown partly as a sectional view.

FIG. 19 is a method of using the gripping head in FIG. 18.

FIG. 20 is another method of using the gripping head in FIG. 18.

FIG. 21 is an embodiment of the fastening member of the gripping head in FIG. 18.

FIG. 22 is a third method of using the gripping head in FIG. 18.

FIG. 23 is a fourth method of using the gripping head in FIG. 18.

FIG. 24a is a schematic view of a superior portion of the spinal column at the chest (thorax) and a preferred method of using a gripping member according to the invention and a preferred method of using a gripping head according to the invention.

FIG. 24b is a schematic view of a superior portion of the spinal column at the chest (thorax) and a preferred method of using a gripping member unit according to the invention.

FIG. 25a is a schematic view of an inferior portion of the spinal column at the lumbar area (lumbus) and preferred methods of using two different gripping members according to the invention.

FIG. 25b is a schematic view of an inferior portion of the spinal column at the lumbar area (lumbus) and another preferred method of using the gripping member in FIG. 25a.

FIG. 26 is a schematic side view of a portion of the spinal column and a preferred method of using a gripping member according to the invention.

FIG. 27 is a side view of a mechanically adjustable spinal therapy apparatus.

FIG. 28 is a perspective view of the spinal therapy apparatus in FIG. 27.

FIG. 29 is a perspective view of a fourth preferred embodiment of a gripping member unit according to the invention, which embodiment has been formed into a hand-held pressing device.

FIG. 30 is a schematic side view of the height adjustment in an embodiment of the gripping member.

FIG. 31 is a perspective view of a fifth preferred embodiment of a gripping member unit according to the invention.

FIG. 32 is the gripping member unit in FIG. 31 with attached shafts functioning as handles.

FIG. 33 is a side view of the gripping member unit in FIG. 32.

FIG. 34 is a perspective view of a sixth preferred embodiment of the gripping member unit.

FIG. 35 is a top view of the gripping member unit in FIG. 34 with attached shafts functioning as handles.

FIG. 36 is a side view of a gripping member according to the invention with a gripping head and a shaft.

FIG. 37 is a perspective view of the gripping head and its fastening screw.

FIG. 38 is a schematic view of the gripping head and one vertebra of the spinal column.

FIG. 39 is a side view of a seventh preferred embodiment of the gripping member unit.

FIG. 40 is a top view of the gripping member unit in FIG. 39.

FIG. 41 is a top view of an eighth preferred embodiment of the gripping member unit.

FIG. 42 is a perspective view of a ninth embodiment of the gripping member unit.

FIG. 43 is a front view of the gripping member unit in FIG. 42.

FIG. 44 is a top view of the gripping member unit in FIG. 42.

FIG. 45 is a perspective view of a tenth preferred embodiment of the gripping member unit.

FIG. 46 is a front view of the gripping member unit in FIG. 45.

FIG. 47 is a perspective view of an eleventh preferred embodiment of the gripping member unit.

FIG. 48 is a top view of the gripping member unit in FIG. 47.

FIG. 49 is a top view of a twelfth preferred embodiment of the gripping member unit.

FIG. 50 is a top view of yet another embodiment of the gripping member unit.

FIG. 51 is a schematic side view of a gripping member according to the invention equipped with a shaft, pressed against the back of the person using the apparatus.

FIG. 52 is the gripping member in FIG. 51 in another position and pressed against the back of the person using the gripping head of the apparatus.

Figure 1:
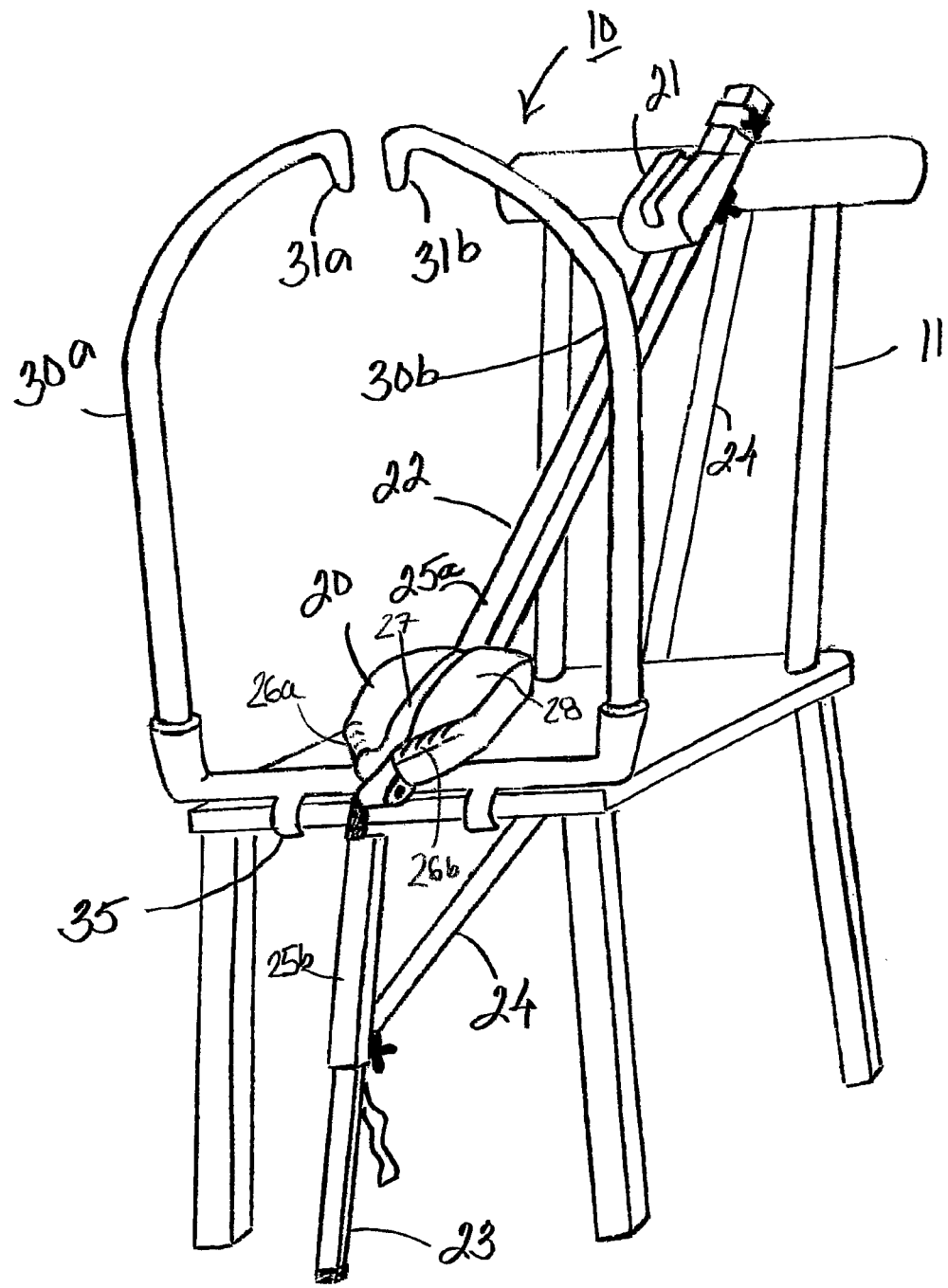
FIG. 1 shows a spinal therapy apparatus 10 according to the invention, the apparatus being fastened to a chair 11 with a fastening strap 24 and hooks 35. A rubber coating is used in places where the spinal therapy apparatus 10 and the chair 11 are in contact with each other. It is preferable to place the chair 11 against a wall, and a mat of cellular rubber or the like may used, fixed in front of the chair. The spinal therapy apparatus 10 includes a linking frame 22, to which a lower gripping member unit 20 has been fastened by means of a Velcro fastener and an upper gripping member unit 21 by means of a tightening screw, and floor rest 23 and shafts 30a and 30b, which in this embodiment function as handles. The lower gripping member unit 20 is in this embodiment pad-like in form so that, in the middle of the pad, there is a groove 27 parallel to the user's spinal column and on both sides of it, at the lower edge of the pad, two ridges, which form gripping members 26a and 26b. Further up in the pad, there is also a two-part support part 28 providing support for the back. According to the invention, the ridges 26a and 26b of the gripping members are set at an angle of less than 180°, in which case the ridges form gripping members which are anatomically suitable for all vertebral interspaces of the spinal column, and with the help of these gripping members, each vertebra can be treated separately. Various embodiments of the gripping member unit and the gripping members are shown in the figures below.

In the spinal therapy apparatus in FIG. 1, the gripping member unit 20 is most preferably at sitting height, i.e. approximately 30-70 cm from the floor. The linking frame 22, the lower part of which is gently curved, can be turned upside down, in which case the lower pad, i.e. the lower gripping member unit 20 can be adjusted to two different positions, depending on the height of the backrest of the chair. There is a quick-release joint in the linking frame 22 above the lower gripping member unit 20. The length of the floor rest 23 is also adjustable so that the spinal therapy apparatus 10 can be easily fastened to chairs 11 of various sizes and shapes. There are paddings 25a and 25b on the linking frame 22 as well as on the floor rest 23, against which paddings the person using the spinal therapy apparatus 10 can lean.

Because the lower pad, i.e. the lower gripping member unit 20 and the upper pad, i.e. the upper gripping member unit 21 of the spinal therapy apparatus 10 in FIG. 1 are attached with a movable fastening system, their locations and therefore also the distance between them can be adjusted. The lower gripping member unit 20 and the upper gripping member unit 21 can also be turned to another position and they can be replaced by a gripping member unit of a different size. The upper gripping member unit 21 can also be turned 180° so that its upper end is directed downwards. Since one edge of the upper gripping member unit 21 is slightly higher than the other edge, the higher edge can be placed either on the down side or on the up side by turning the upper gripping member unit 21. On the other hand, in a simple solution, the upper gripping member unit may also be a permanent part of the backrest. In one embodiment of the invention, the upper gripping member unit 21, i.e. the upper pad, is in principle similar to the lower gripping member unit 20. In such a case, the angle of the gripping members in one or both of the pads can be adjusted relative to the midline.

In the spinal therapy apparatus 10 in FIG. 1, the handles 30a and 30b are essentially upwards-directed, curved support rods tilted slightly forward and to the side, which support rods are joined to the frame of the spinal therapy apparatus 10 so as to be rotatable by means of a tapered lock bushing. The rod joining the lock bushings may be fixed or telescopically adjustable in the lateral direction, in which case the spinal therapy apparatus is suitable for both slim and sturdy users. At the ends of rods 30*a* and 30*b*, there are rounded and most preferably also padded end portions 31. The handles 30*a* and 30*b* can be detached so that they can be used as shafts, and the gripping heads 31 on their ends can also be used separately for massaging and mobilising the back, i.e. restoring the mobility of the spinal vertebrae, or for locating trigger points and painful areas.

When using the spinal therapy apparatus 10 in FIG. 1, the user grips the handles 30*a* and 30*b* and leans against the restraint pads of the spinal therapy apparatus, i.e. the gripping member units 20 and 21, and against the padding 25 on the linking frame 22. Thereafter, the person moves and relocates him-/herself by a rocking or sliding motion in the vertical direction so that the required area of the spinal column is pressed against the required point on either of the gripping member units 20 and 21. The gripping member units 20 and 21 are padded and shaped so that they can be used to press and suspend the required area of the spinal column, which area may be located between spinal vertebrae or on a vertebra or to its side, for example.

The operations carried out in such a case include most preferably traction, i.e. lengthwise stretching of the spinal column, extension, i.e. stretching of the spinal column backwards, and rotation, i.e. rotational movement of the spinal column. These operations are controlled by movements of the feet and the pelvis.

Figure 2:
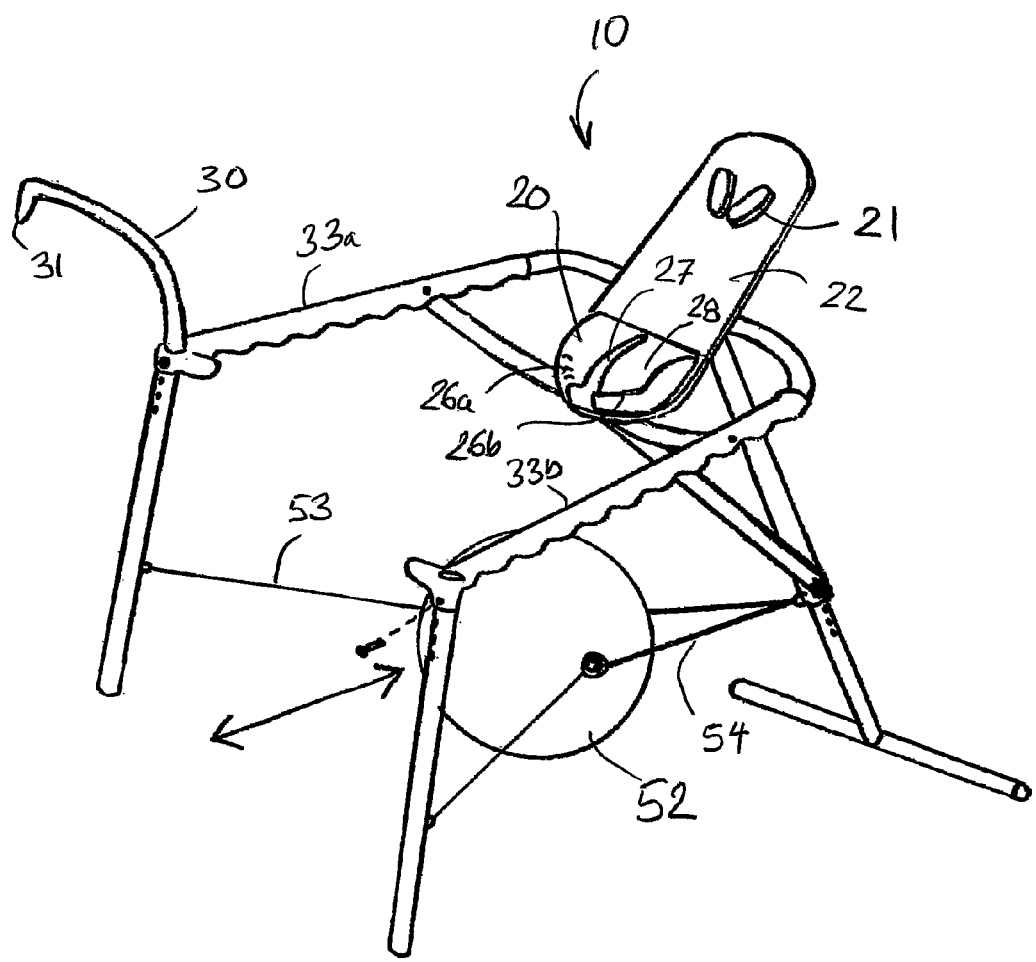

The spinal therapy apparatus 10 in FIG. 2 has handles 30*a* and 30*b* and a rack, by means of which the user of the spinal therapy apparatus 10 can easily move him-/herself to the required position relative to the gripping member units 20 and 21 and lean on the spinal therapy apparatus in various ways and at various heights. This embodiment of the invention also has a ball 52 filled with air, on which the user can sit. The hardness of the ball 52 can be adjusted by regulating the pressure of the air contained in it. The person using the apparatus can lower him-/herself supported by the ball 52, in which case the ball 52 will roll between the body and the floor. The movement of the ball 52 is restricted by strings 53, and the ball can be restored to its initial position by pulling a rubber band 54.

Figure 3:
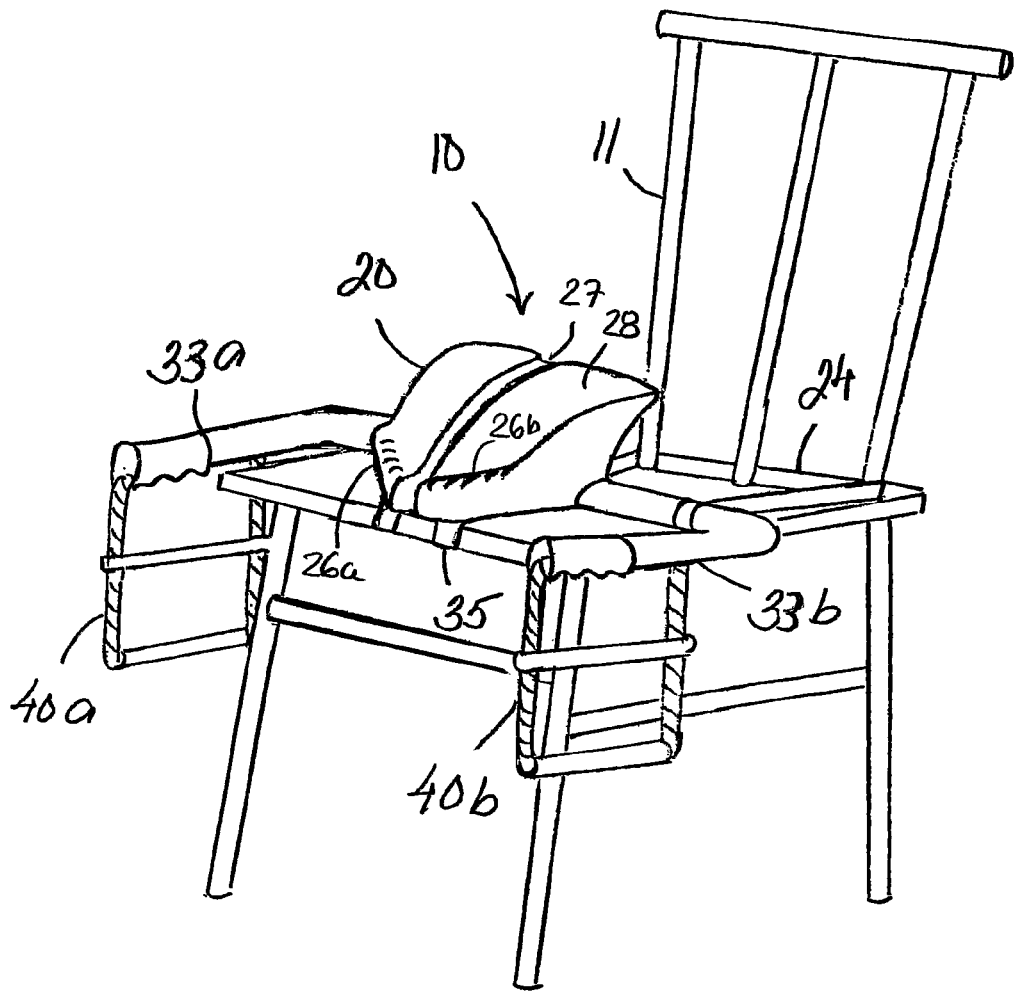

FIG. 3 shows a simple embodiment of the spinal therapy apparatus 10, which includes only a lower gripping member unit 20 and handles 33*a* and 33*b* permanently attached to it. The apparatus 10 is attached around the backrest of a chair 11 by means of a strap 24. There are hooks 35 at the front edge of the lower gripping member unit 20, which hooks rest on the front edge of the seat of the chair 21. As an additional fitting, rope handles 40*a* and 40*b* may be attached to the handles 34*a* and 34*b* of the apparatus 10, in which case the user may change the position of his/her grip in the vertical direction as required.

Figure 4:
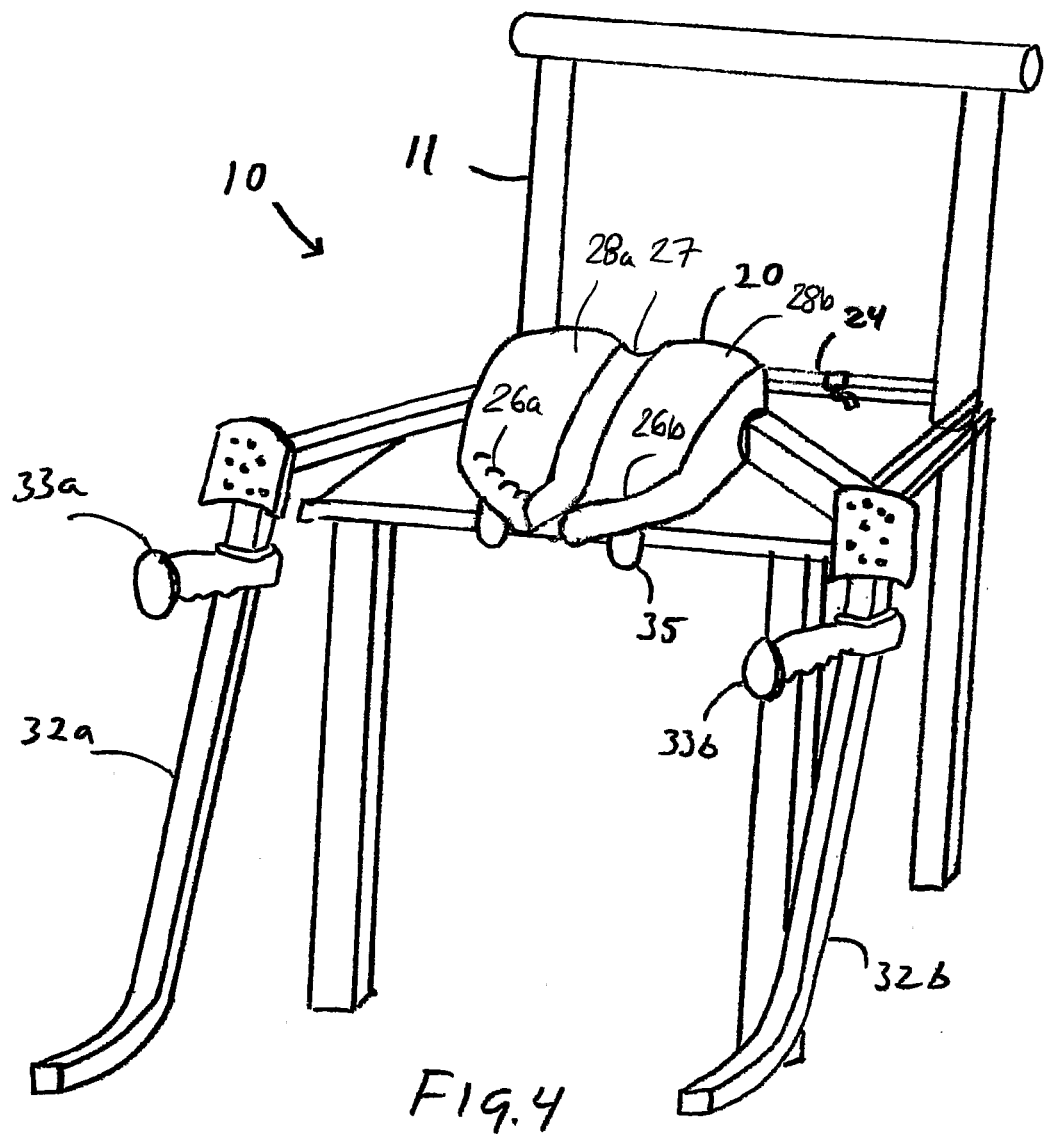

The spinal therapy apparatus 10 with two additional supports 32*a* and 32*b* shown in FIG. 4 is also fastened around the backrest of a chair 11 by means of a strap 24. However, the spinal therapy apparatus 10 may also be fastened to the seat of the chair 11 by means of a floor rest 23 in the middle in front of the seat of the chair. The additional handles 33*a* and 33*b* are attached to the additional supports 32*a* and 32*b*, where they can be easily moved to the required height. The additional supports 32*a* and 32*b*, which in FIG. 4 are bent at the lower end to increase the stability of the apparatus, are most preferably made of square tube, also in the embodiments shown in other figures. In such a case, the additional handles 33*a* and 33*b* can be turned and directed in the required direction, for example forward or to the side. The additional supports 32*a* and 32*b* are attached to the gripping member unit 20 in such a way that their ends can turn freely against the floor 15.

Figure 5:
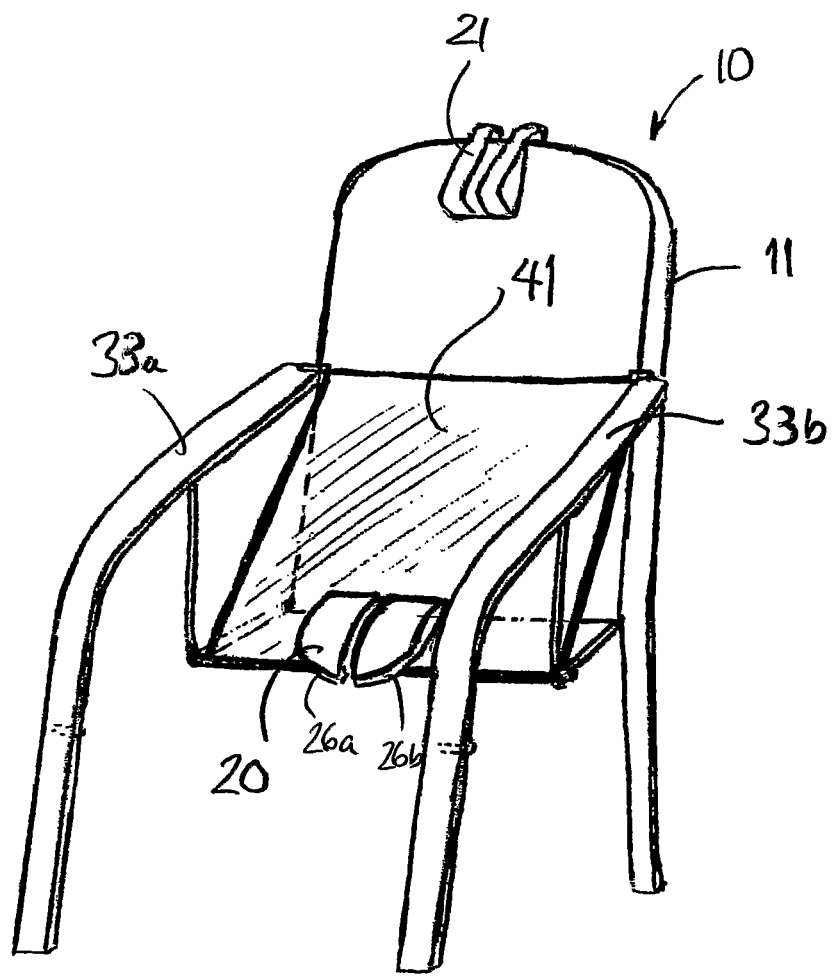

FIG. 5 shows a spinal therapy apparatus 10 attached to the structure of a chair 11. A lower pad, i.e. a lower gripping member unit 20 is fastened to the seat 41 of the chair 11 so that, when the user sits in the chair in a normal manner, the pad is below the seat 41. In FIG. 5, the lower gripping member unit is drawn with broken lines in this position and indicated by the reference number 20*a*. The spinal therapy apparatus 10 is brought to working order by turning the seat 41 upside down and setting it to an angle of approximately 45°. In such a case, the lower gripping member unit 20 comes up and is positioned on the lower part of the seat 41. An upper pad intended for the treatment of the thoracic spine and the neck, i.e. an upper gripping member unit 21 is fastened to the upper edge of the backrest of the chair 11.

Figure 6:
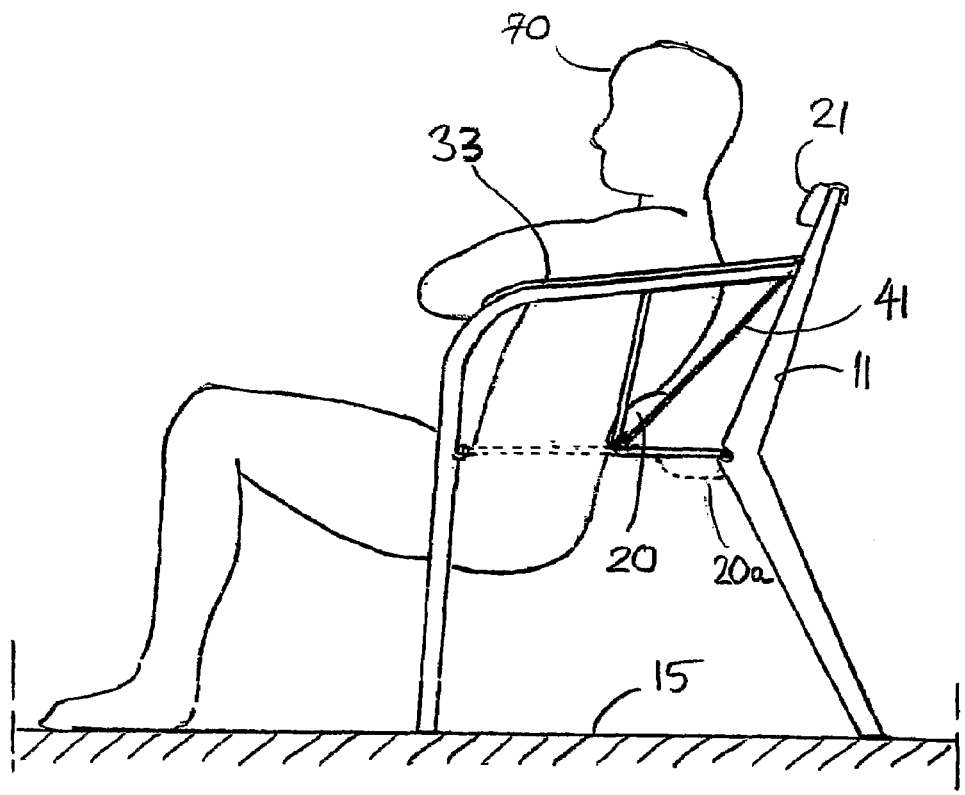

FIG. 6 shows a method of using the spinal therapy apparatus 10 attached to the structure of a chair 11, according to FIG. 5. The spinal therapy apparatus 10 has been brought to working order in the manner described above, and the user of the spinal therapy apparatus leans his/her arms on the armrests 30 of the chair 11, the armrests now functioning as arm supports of the spinal therapy apparatus 10. Leaning on the armrests 30, the user can now gradually lower him-/herself so that each vertebral interspace in the spinal column to be treated is always level with the lower gripping member unit 20 as appropriate. The armrests 30 can made so as to be telescopically extendable forward, in which case it is even easier to use them because in this way, the entire length of the arms can be used.

Figure 7:
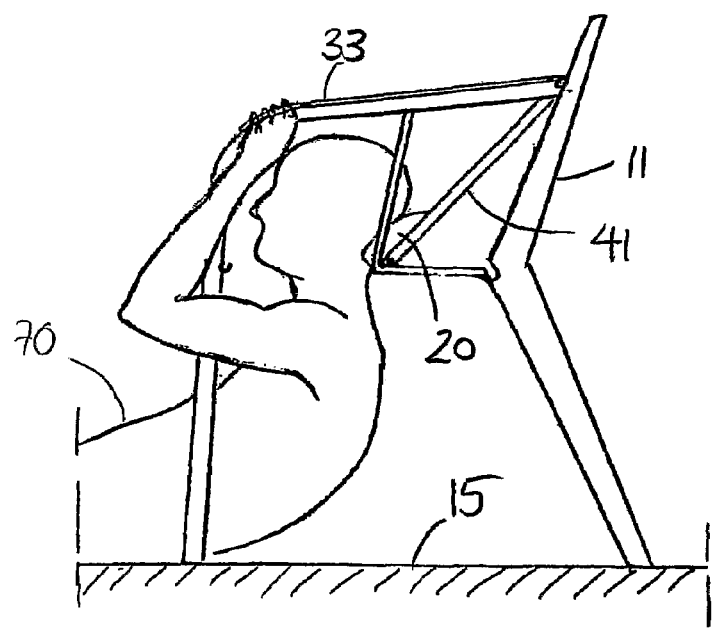

FIG. 7 also shows how the neck area can be treated using the lower gripping member unit 20. In such a case, the support part supports the back of the head.

Figure 8:
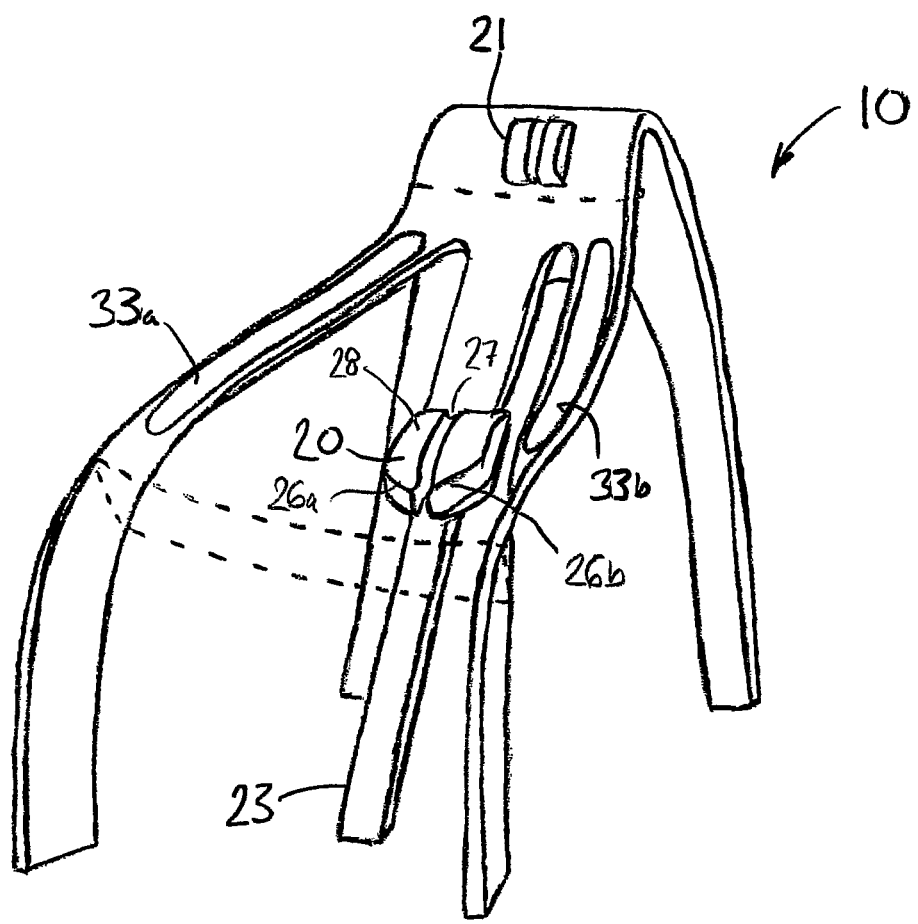

FIG. 8 shows an embodiment of the spinal therapy apparatus 10 wherein a lower gripping member unit 20 and an upper gripping member unit 21 are fastened to a floor rest 23. On both sides of the floor rest, there are two padded handles 30*a* and 30*b* extending to the floor, which padded handles also provide arm supports, against which arm supports the user can lean the entire length of his/her arms, from the palm up to the shoulders. These supports can also tilted inwards or outwards to improve the grip, or they can also be horizontal. With a detachable fabric cover, it can also function as a chair when the spinal therapy apparatus is not in use.

Figure 9:
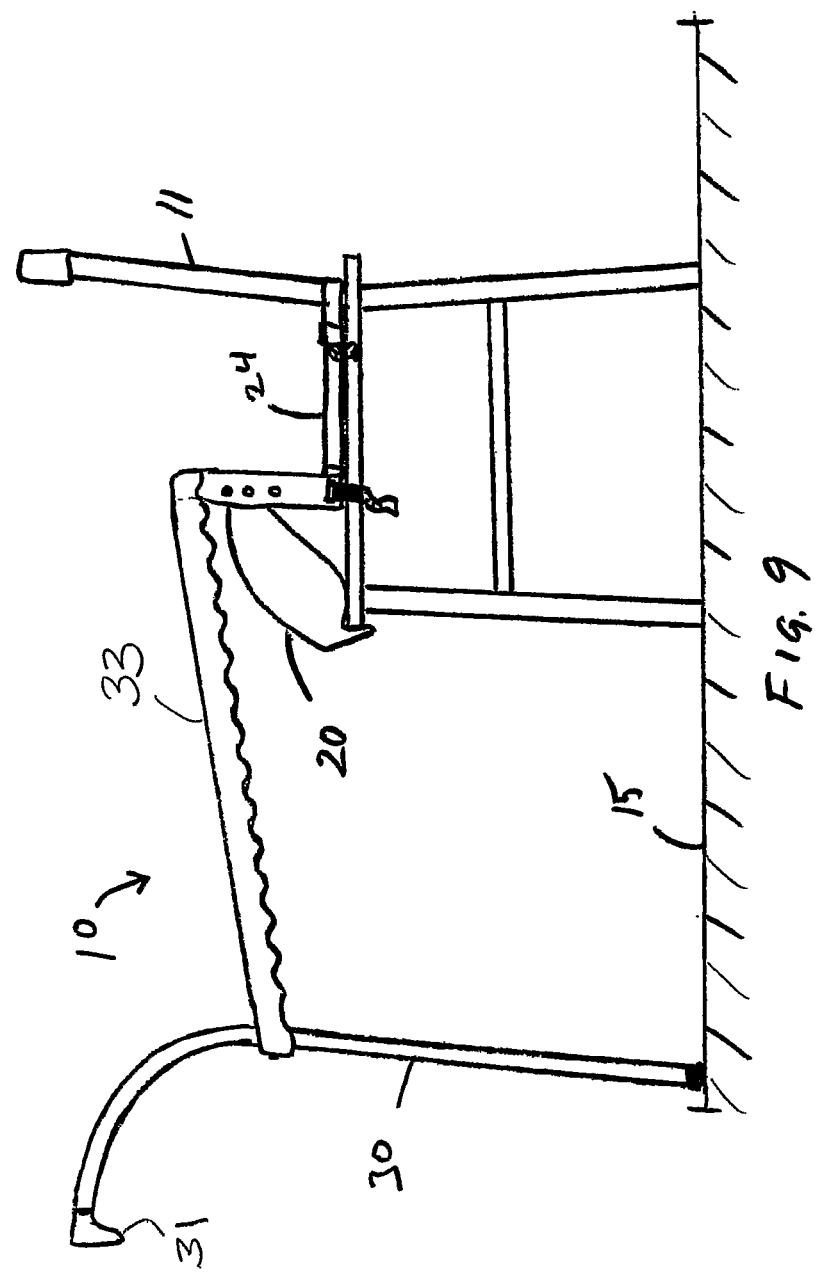

FIG. 9 shows yet another embodiment of the spinal therapy apparatus 10 with horizontal, extended handles 33.

Figure 10:
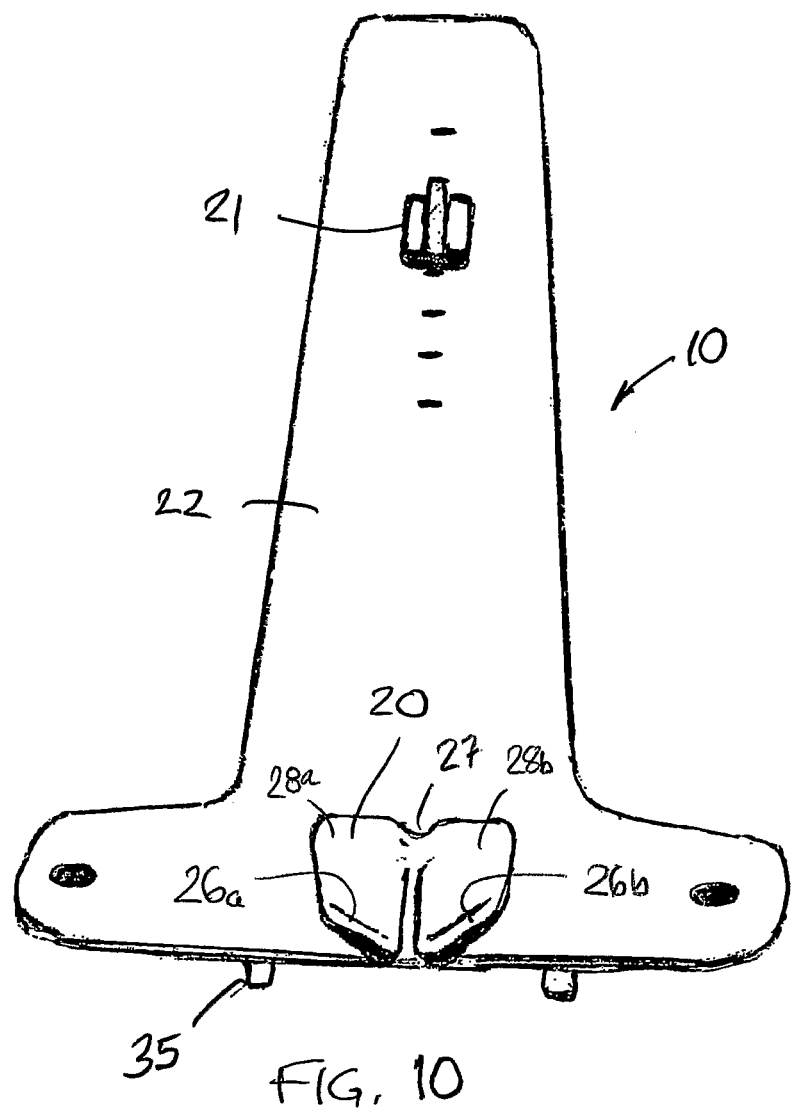

FIG. 10 shows one embodiment of the spinal therapy apparatus 10 where gripping member units 20 and 21 are disposed on a plate-like linking frame 22, wherein hooks 35 rest on the front edge of the seat of a chair. The upper fastening is arranged by means of a strap or hooks. The construction of the spinal therapy apparatus 10 may also be such that the linking frame 22 and at least one of the gripping member units 20 and 21 are formed from one and the same cast component.

Figure 11:
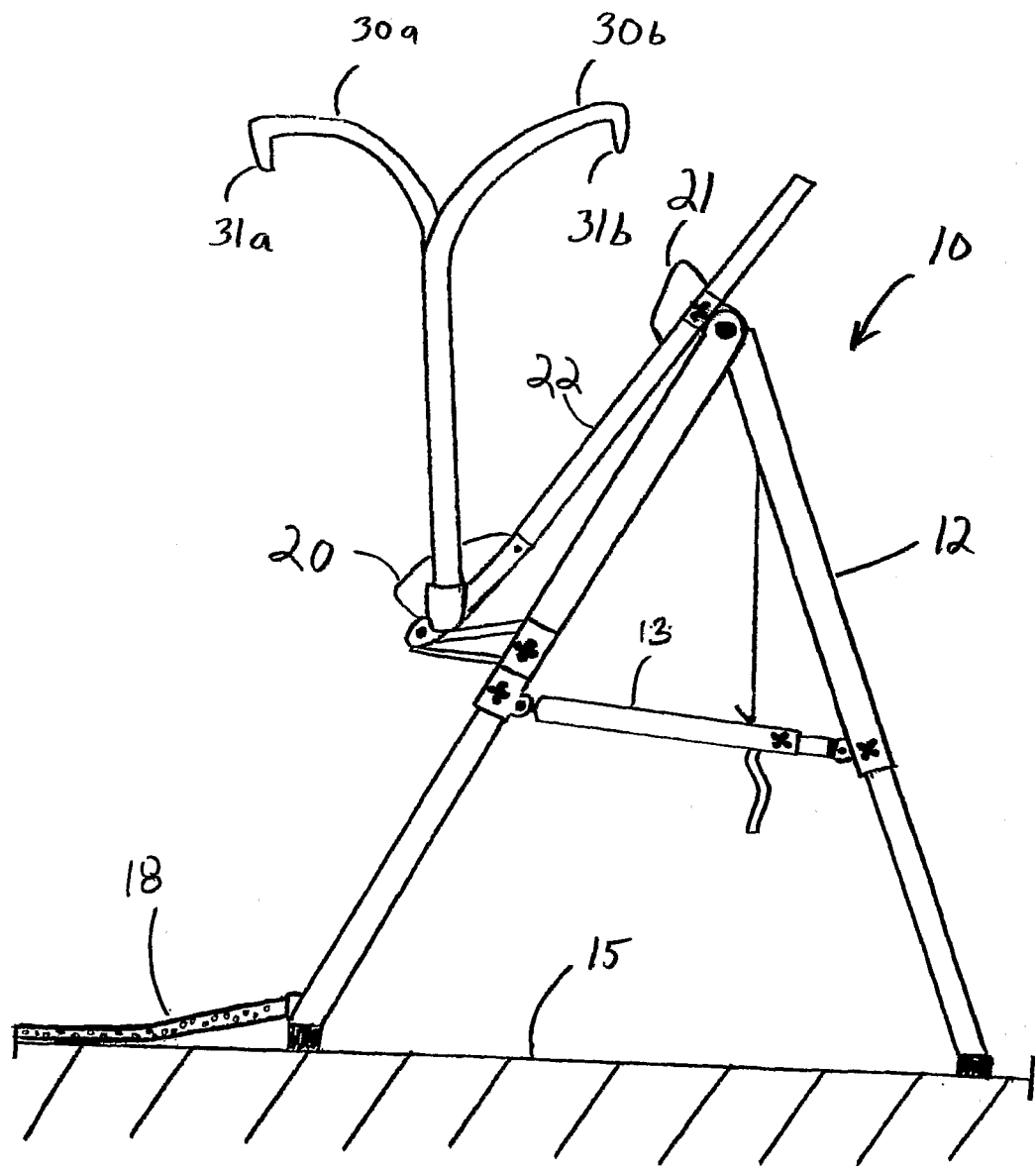

FIG. 11 shows a spinal therapy apparatus 10 which has a support rack 12. In such a case, the apparatus does not have to be fastened to a chair or a similar object, but stays in its place on the floor 15 on its own support legs. The legs of the support rack 12 and the linking rod 13 between them are adjustable, so that a lower gripping member unit 20 and an upper gripping member unit 21 attached to them can always be set at the required height from the ground. The position of the linking frame 22 can also be adjusted, and the lower gripping member unit 20 and the upper gripping member unit 21 can thus be set at the required angle relative to the horizontal plane. The linking rod 13 can function as a floor rest in a case where the linking frame portion of the spinal therapy apparatus 10 is detached and used with a chair, when travelling for example.

Figure 12:
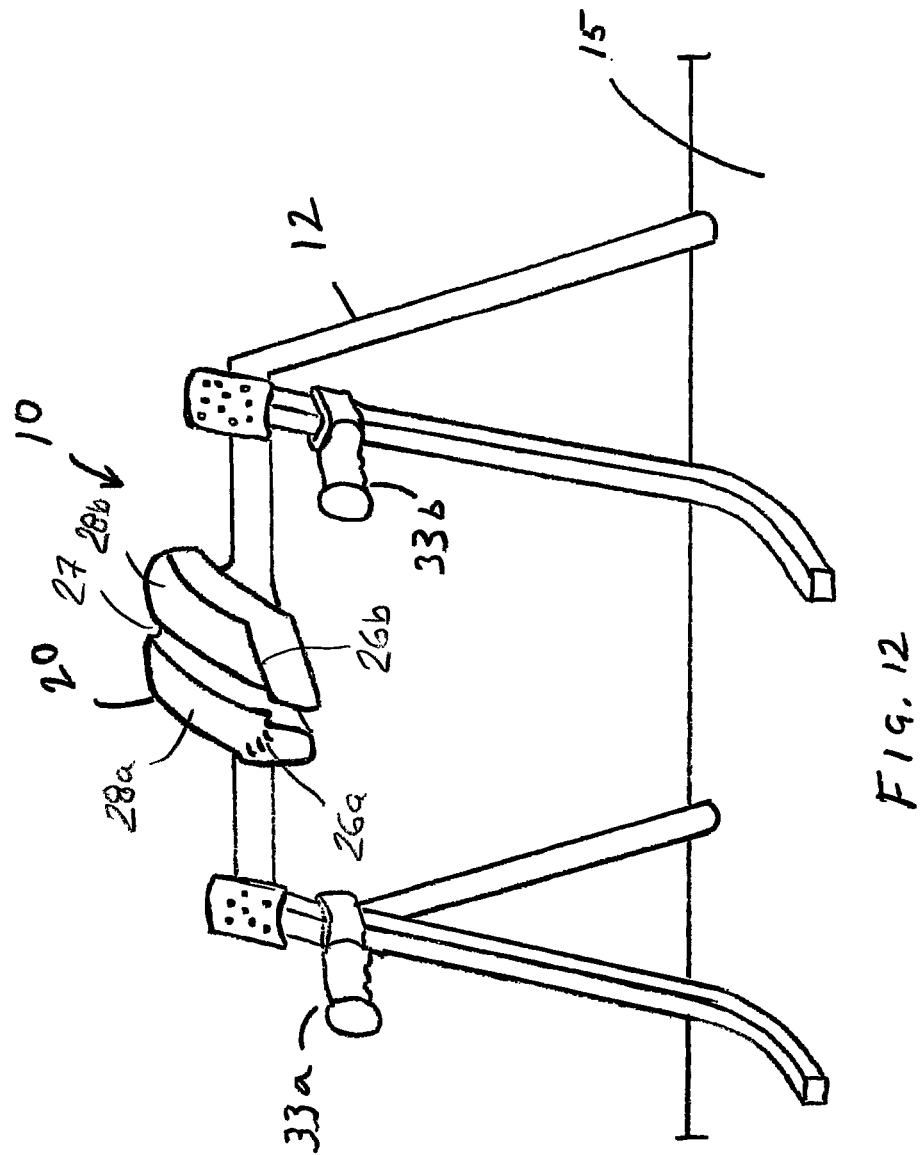

FIG. 12 shows a foldable spinal therapy apparatus 10 where a lower gripping member unit 20 and handles 30a and 30b are attached to a support rack 12 resting on its own feet. The front feet of the apparatus are curved at their lower end to increase stability, and the top ends of the feet are provided with padding.

Figure 13:
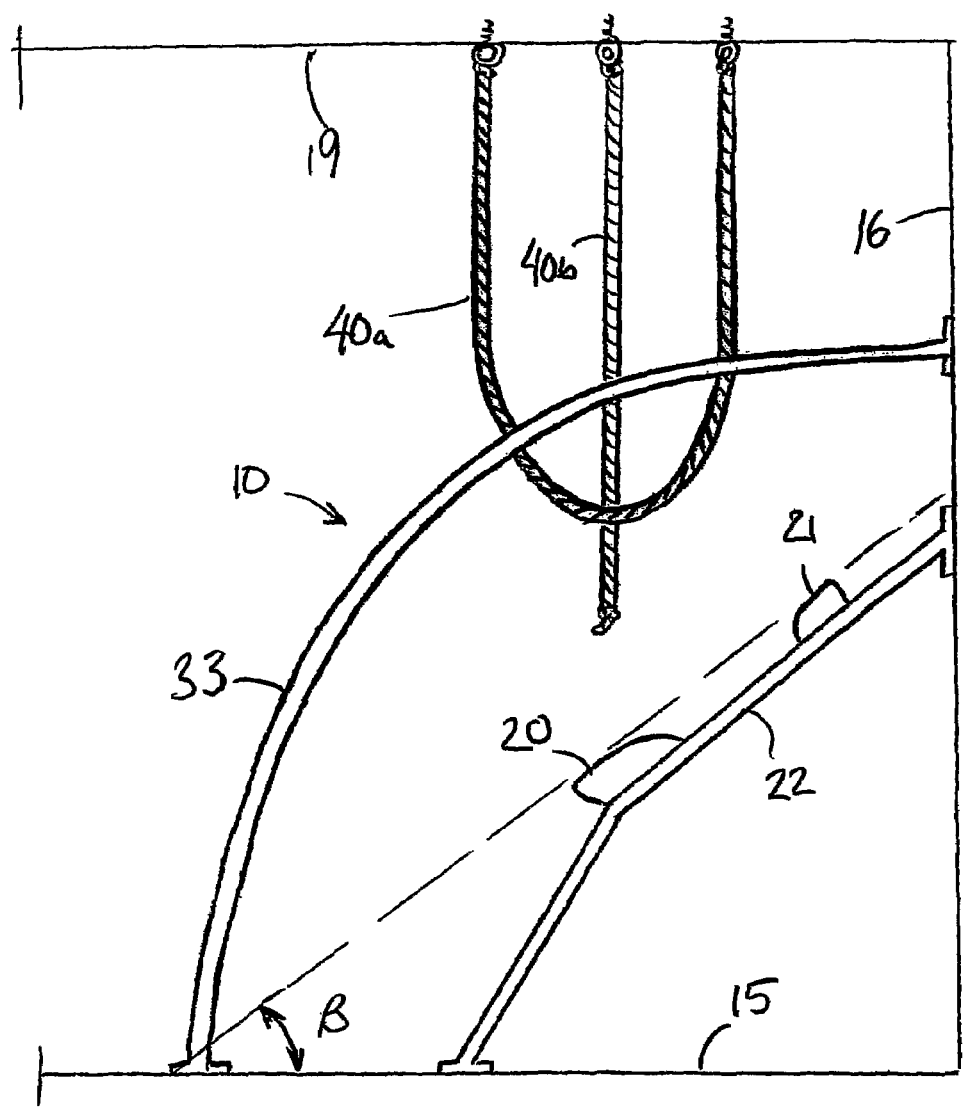

FIG. 13 shows an embodiment of the spinal therapy apparatus 10 that is permanently installed in a home or gymnasium, for example. The frame of the spinal therapy apparatus 10 is provided by a rod 22 or a plate with padding, the lower end of which rod or plate is fastened to the floor 15 and the upper end to the wall 16. A lower gripping member unit 20 and an upper gripping member unit 21 are attached to the rod, and their location on the rod 22 can be changed. In the spinal therapy apparatus 10 in FIG. 13, there are one or two handles 30, which are also attached both to the floor 15 and the wall 16.

Also indicated in the apparatus 10 in FIG. 13 are alternative rope handles 40a or 40b, which can be fastened to the ceiling 19, and the reclining angle β, i.e. the principal angle at which the spinal column of the person using the spinal therapy apparatus 10 is in relation to the floor plane 15. The reclining angle is, for example, 30°-70° and most preferably 40°-50°.

Figure 14:
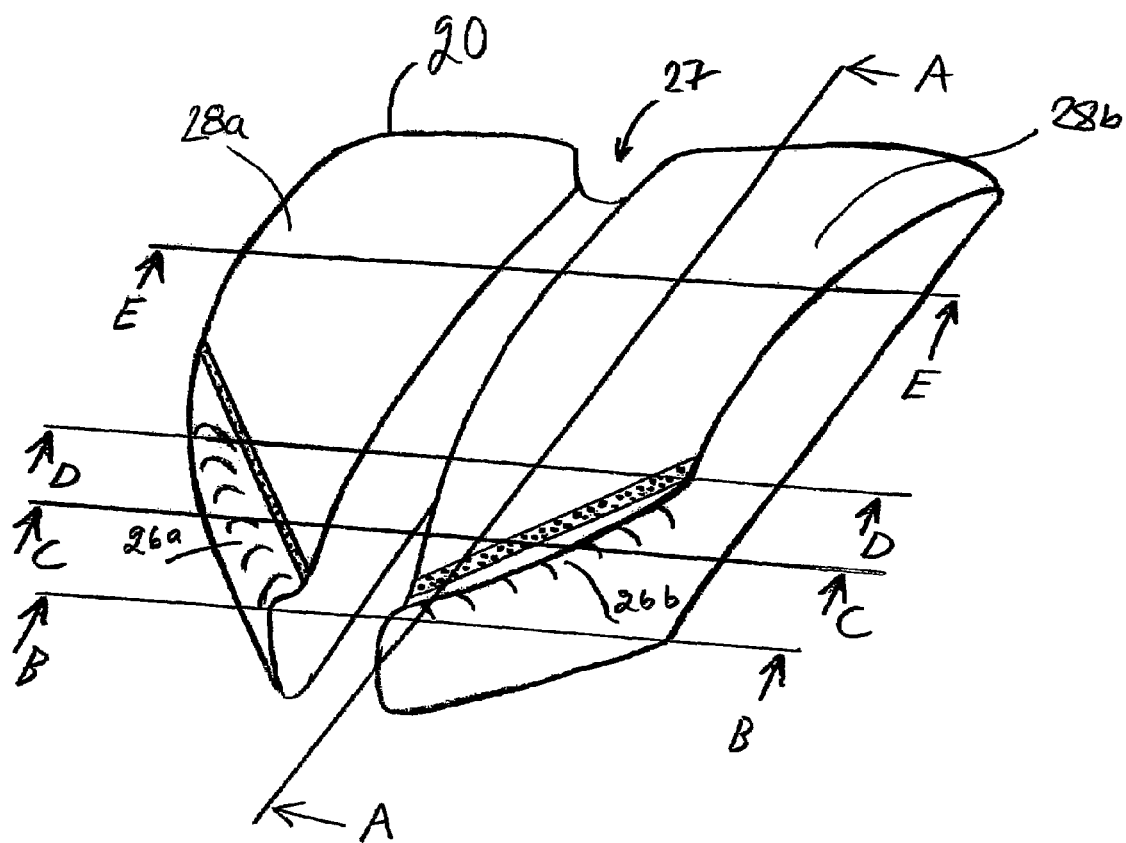

FIG. 14 shows a perspective view of a gripping member unit 20 of a spinal therapy apparatus 10. As shown in the figure, the gripping member unit 20 has two ridges or bulges that form gripping members 26a and 26b. The gripping members 26a and 26b are so shaped that, with their help, a more accurate contact can be achieved, the painful area can be located and thus various areas of the spinal column can be gripped in the desired manner. Further back in the gripping member unit 20, behind the ridges 26a and 26b of the gripping members, there are padded, convex support parts 28a and 28b, which start immediately in the vicinity of the ridges 26a and 26b. Between the support parts 28a and 28b, there is a groove 27, depression or gap extending over the entire length of the gripping member unit 20. Various embodiments of said groove, depression or gap are presented below. There is also a groove between the gripping members 26 and the support parts 28, the purpose of which is described below. The shape of the gripping member unit 20 is described in greater detail with the help of the cross-sectional views shown in FIGS. 15a-15e.

In this embodiment of the invention, between the support parts 28a and 28b, there is a groove 27 extending over the entire length of the gripping member unit 20, which groove ensures that the gripping member unit 20 does not exert pressure on the central portion of the spinal column, i.e. spinous process (processus spinosus). Thanks to the wedge-like tips and the slightly concave front edge of the front portion of the apparatus, the user is also able to apply pressure to the lamina of the lowest lumbar vertebra, between the iliac bones. The tips also make it possible to grip the base of skull and cervical vertebrae when stretching the neck.

Essential parts of the gripping member unit 20 in FIG. 14 are the ridges 26a and 26b of the gripping members, which form an angle relative to each other. The ridges 26a and 26b of the gripping members are so shaped that they are pressed against the lamina of spinal vertebrae, and thus each vertebral interspace in the spinal column can be treated one at a time. The ridges have less padding so as to achieve accuracy and rigidity. Both the ridges and the support part may have exchangeable padding to obtain the required softness.

FIG. 15a shows a cross-sectional view of the gripping member unit 20 of FIG. 14. As shown in the figure, the ridge 26 of the gripping member forms a clear bulge at the edge of the gripping member unit 20. Using the ridge 26 of the gripping member unit, one can apply pressure to the required area between spinal vertebrae or on a vertebra or to its side. When treating spinal vertebrae, one can think of the ridges 26a and 26b of the gripping member unit as suspending the vertebra and of convex support parts 28a and 28b as a support part and as a widening that provides a seat of sorts when starting spinal therapy. FIGS. 15b-15e show cross-sectional views of the gripping member unit 20 in FIG. 14 at various locations in it.

Figure 16A:
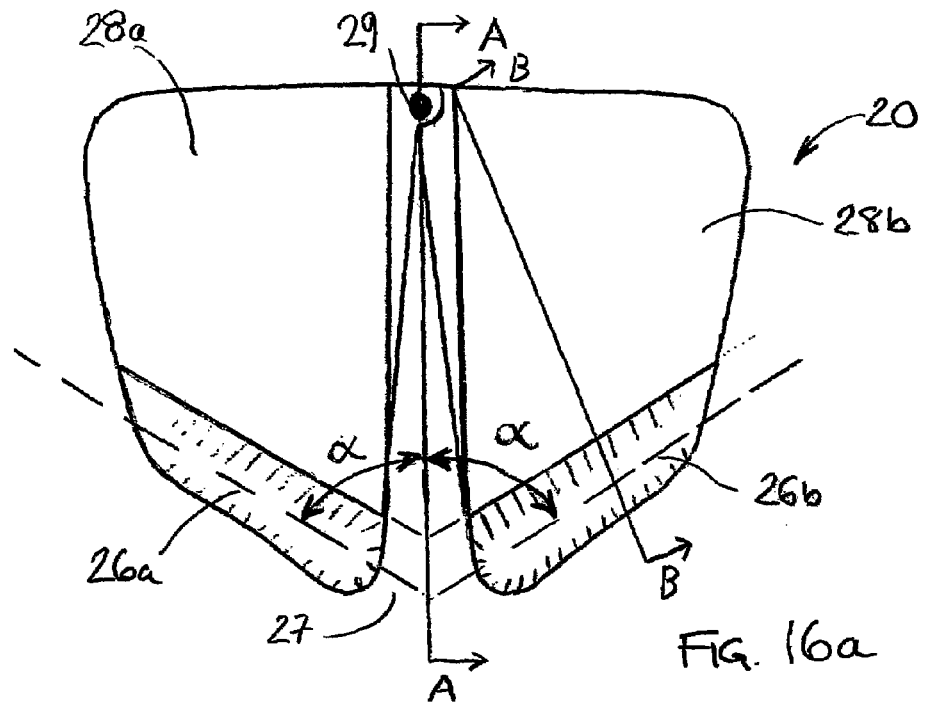

FIG. 16a shows a top view of one embodiment of the gripping member unit 20. As shown in the figure, support parts 28a and 28b and pointed ridges 26a and 26b of the gripping members are located in two separate halves. The halves are joined to each other by a hinge pin 29. By turning the halves of the gripping member unit 20 about the hinge pin 29, one can adequately adjust the distance between the ridges 26a and 26b of the gripping members. In this way the gripping member unit 20 can be adjusted to suit different people.

Figure 16B:
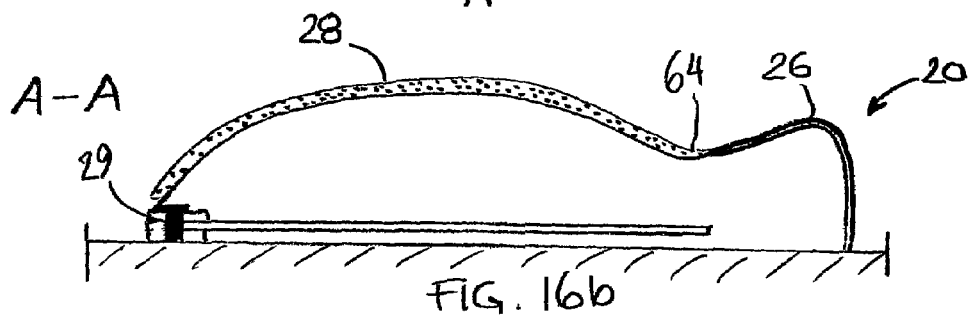
Figure 16C:
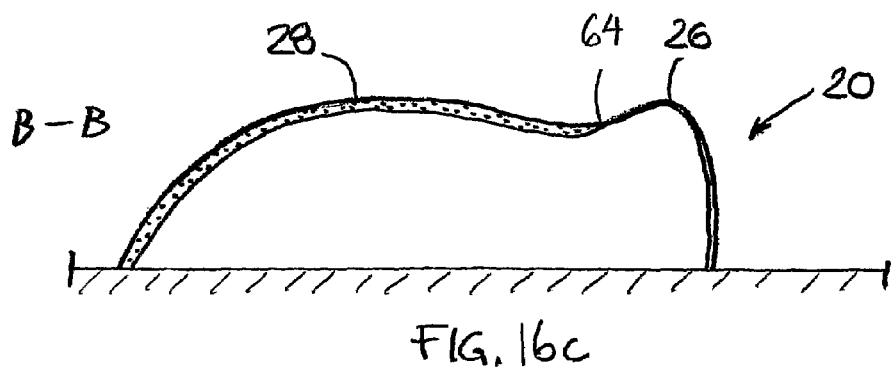

Also indicated in FIG. 16a is angle α of the ridges 26a and 26b of the gripping members relative to the midline of the gripping member unit 20. This angle is at the same time the angle between the midline of the spinal column of the person using the apparatus and the gripping member 26. The angle between both gripping members 26a and 26b of the gripping member unit 20 in such a case is 2α and thus less than 180°. In the embodiments presented here, the angle α is, for example, 15°-80°, most preferably 40°-60°. The angle between both gripping members 26a and 26b is 30°-160°, most preferably 80°-120°. FIGS. 16b and 16c show two cross-sectional views of the hinged gripping member unit 20 of FIG. 16a.

Figure 17B:
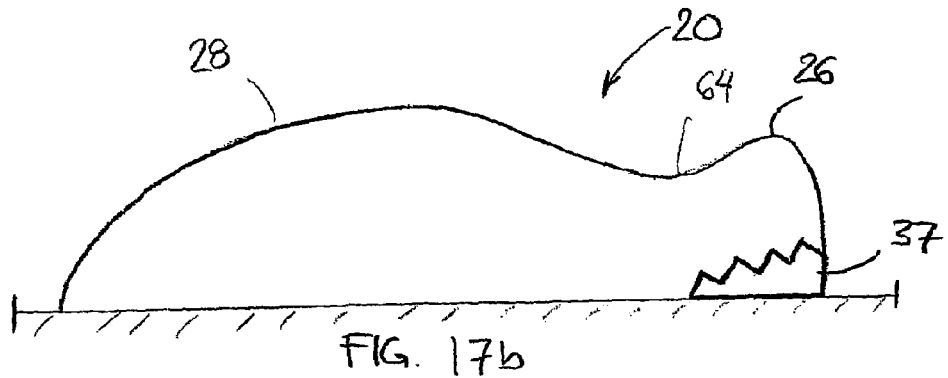
Figure 17A:
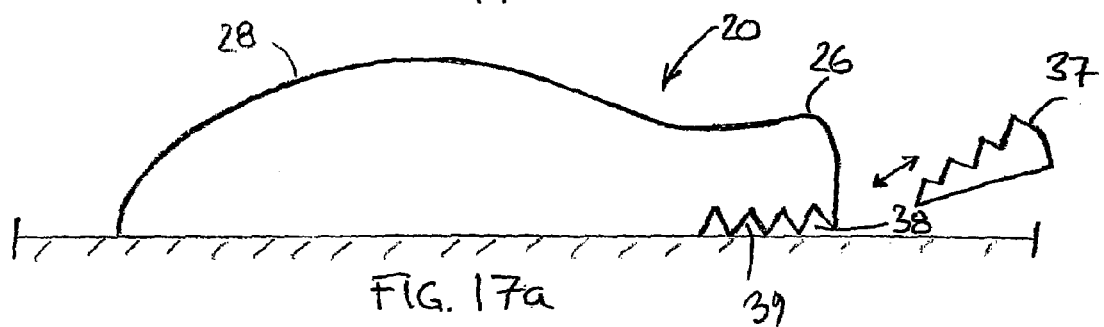

FIG. 17a shows the structure of the gripping member unit 20, wherein a wedge 37 can be pushed under the edge portion of the flexible gripping member unit 20 to adjust the height and the shape of the edge portion of the gripping member unit 20. With the help of the wedge 37, the height and shape of a ridge 26 on the gripping member of the edge portion of the gripping member unit 20 can be adjusted so that, when there is no wedge 37 under the edge portion of the gripping member unit 20, the edge of the gripping member unit 20 is low or substantially flat.

In FIG. 17a, the wedge 37 functioning as an adjustment piece can consist of a single component, in which case it can affect both halves of the gripping member unit 20, or there may be two wedges, in which case each wedge 37 affects the height and shape of one half of the gripping member unit 20 only. If there are two wedges 37, it is possible to adjust both halves of the gripping member unit 20 separately. If one of the wedges 37 is inserted deeper into the space 38, the half of the gripping member unit 20 in question is correspondingly higher. In such a case, it is possible to form two ridges or tips of different heights in the gripping member unit 20, which is preferable particularly in cases of scoliosis.

FIG. 17b shows the gripping member unit 20 of FIG. 17a in a situation where the wedge 37 is inserted fully under the gripping member unit 20, in the space 38. It is also possible to insert the wedge 37 under the gripping member unit 20 only partially, in which case, the deeper the wedge 37 is inserted into the space 38 under the gripping member unit 20, the higher the edge of the gripping member unit 20 rises. At the same time, a ridge 26 of the gripping member with adjustable height is formed in the edge portion of the gripping member unit 20. The shape of the edge portion of the gripping member unit 20 can also affect the shape of the ridge 26 being formed in the gripping member.

Figure 17C:
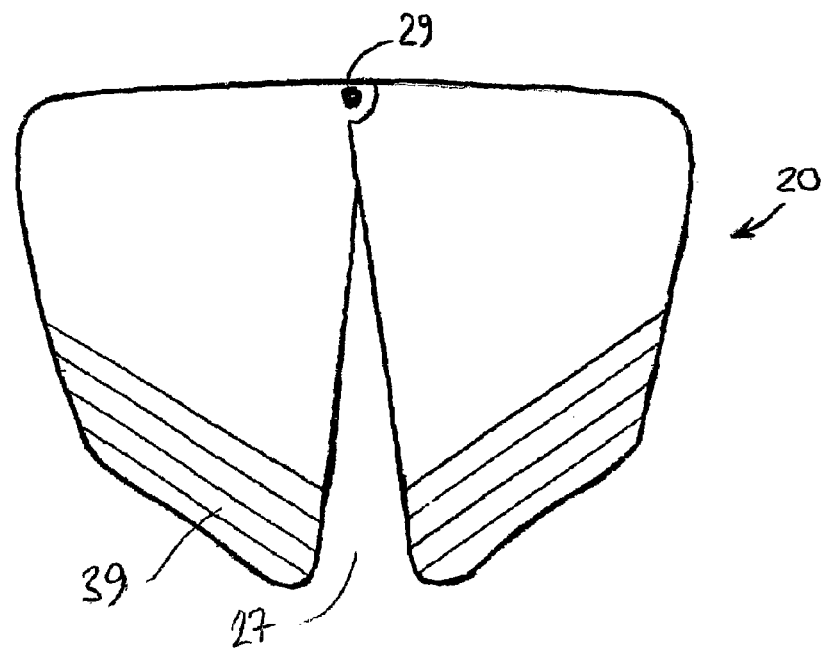

FIG. 17c shows a view from below of one embodiment of the gripping member unit 20, wherein the grooves 39 under the gripping member unit 20 are visible. As shown in the figure, the location of wedges 37 in the grooves 39 under the front edge of the gripping member unit 20 can also be adjusted in the lateral direction. By relocating the wedge 37 to the required locations under the gripping member unit 20, one can adjust the shape and height of ridges 26 of the gripping member of the gripping member unit as required. By making the wedge 37 thicker towards its outer edge also it is possible to affect the angle of inclination of the sides of ridge 26 of the gripping member by moving it in the lateral direction.

FIG. 18 shows a gripping head 31 of the spinal therapy apparatus 10 and its shaft portion 30. The gripping head 31 may also be at least partially padded so that there is a rubber coating 42, which forms the padding, on the gripping head 31, which padding is shown as a cross-sectional view in FIG. 18. The rubber coating 42 can be replaced so that the softness and shape of the surface of the gripping head 31 can always be adjusted as required. In FIG. 18, the shaft portion 30, which can also function as a handle of the spinal therapy apparatus 10, is placed on the floor 15 so that its end is against the floor 15 and the shaft portion 30 forms an angle γ with the floor 15. Thus the gripping head 31 on the end of the shaft portion 30 is vertically disposed. The handle 30 of the spinal therapy apparatus 10 can thus also be used also as a shaft portion in combination with the gripping head 31 or a gripping member 26 separately for massaging or mobilising the back, i.e. restoring the mobility of the spinal vertebrae, or for locating trigger points and painful areas.

As shown in FIG. 18, a person using the shaft portion 30 lies supine so that a vertically disposed gripping head 31 according to this embodiment of the invention at the end of the shaft portion 30 is placed in contact with the area of the back to be treated. In such a case, even a light movement of the hand is sufficient to apply force from the curve of the shaft portion 30 via the floor 15 to the required area. The shaft portion 30 and the gripping head 31 attached to it can also be used for stretching the back of the legs.

FIG. 19 shows both handles 30a and 30b of the spinal therapy apparatus 10 detached so that they can be used as shaft portions of the gripping heads 31. In such a case, the shaft portions 30a and 30b are connected with each other by a connecting strap 44 and placed on the floor 15 so that gripping heads 31a and 31b at the ends of both the shaft portions are vertically disposed. The gripping heads 30a and 30b can in this way be used for massaging, mobilising spinal vertebrae or locating trigger points and painful areas simultaneously or one after another while the other is in a horizontal position.

FIG. 20 shows a method of using the shaft portion 30 and the gripping head 31 for rotational stretching of the lumbar spine or the thoracic spine. Greater rotational force can be applied by connecting the strap of the spinal therapy apparatus with the shaft portion 30 by means of a knot or a bushing and by anchoring the buckle end of the strap between a door and its frame, for example, or around a pillar, for example. The user 70 of the apparatus lies down on a mat 18 with the side of the body to be stretched, i.e. the more painful side, against the mat. After this he/she places the gripping head 31 at the lamina of the inferior vertebra, above the line formed by the spinous processes, in the vertebral interspace to be treated. Thereafter he/she keeps his/her lower hand on the knot/bushing and thus increases its friction and rotates his/her upper body by reaching back with the upper hand and shoulder. This efficiently expands the openings of the nerve roots and stretches the tissue on the side of the spinal column against the floor. Relocating the knot or bushing on the shaft provides a rapid method of finding an optimal distance to the anchoring point without the user having to move his/her entire body. This method can be used for the lumbar spine and inferior portions of the thoracic spine. The user can have an additional weight 14 in his/her upper hand.

Figure 21:
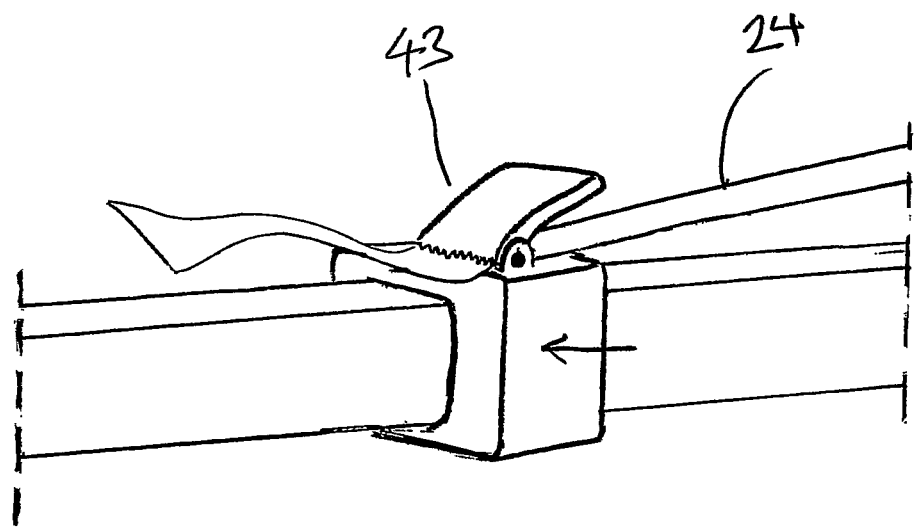

FIG. 21 shows one method of securing a strap 24 belonging to the spinal therapy apparatus, wherein a frictional bushing 43 is connected with the strap 24.

Figure 22:
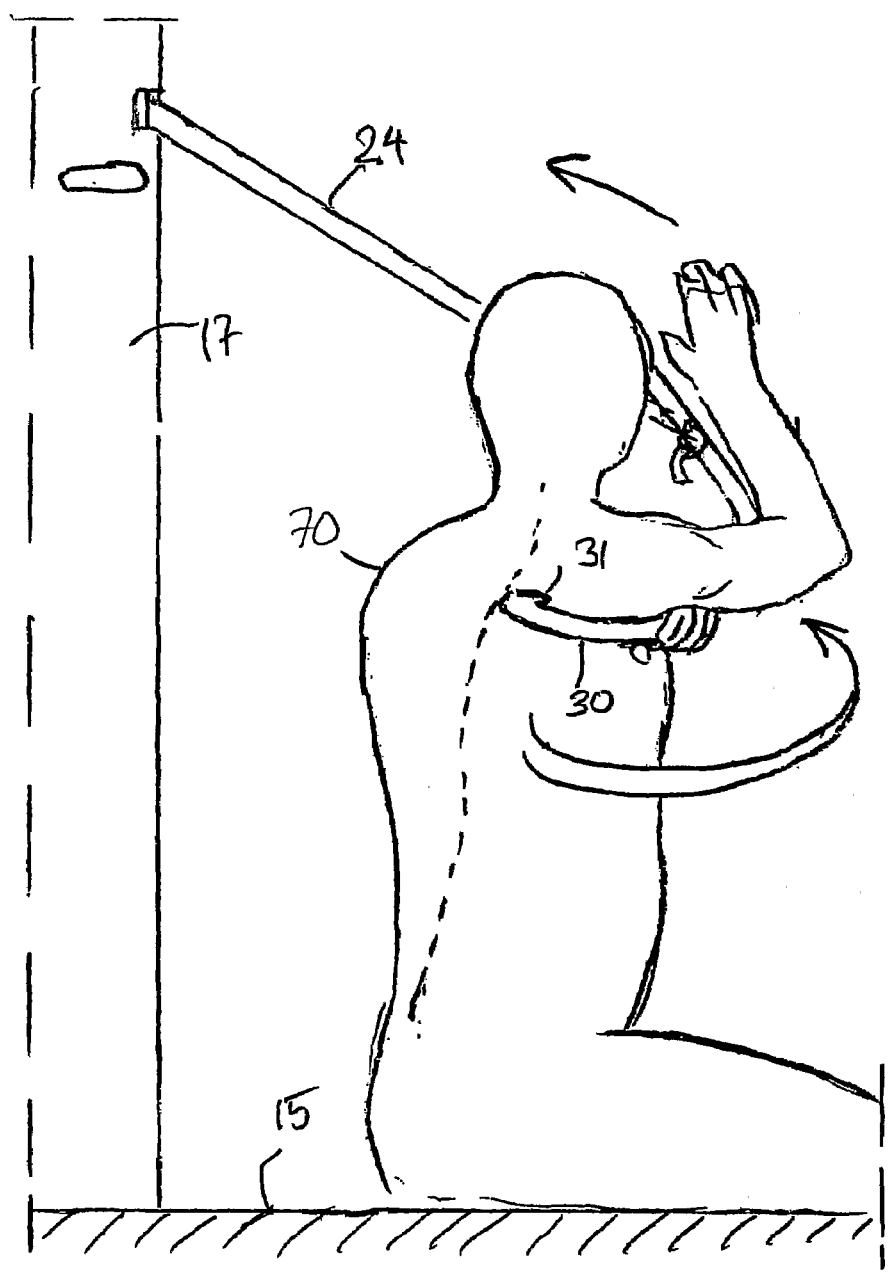

FIG. 22 shows rotational stretching of a superior portion of the thoracic spine. When rotating a vertebra in the superior portion of the thoracic spine, the person is in a sitting or standing position and grips the shaft portion 30 of a gripping head 31 with the hand on his/her healthy side and brings the gripping head over the chest and further under the elbow or alternatively over the shoulder, depending on the location of the area to be treated. The gripping head 31 is positioned above the painful area, on the lamina/processus transversus, and the handle is tightened up against the body as rigidly as possible. Simultaneously, the user starts to rotate his/her upper body away from the painful area and at the same time stretches the arm on the painful side, holding the arm straight, parallel to the shaft of the handle, over the chest. The motion can be made more effective by anchoring the apparatus by its strap to a door, etc.

FIG. 23 shows stretching of the calf, back of the thigh and/or sole of the foot using the shaft portion 30 and gripping head 31 of the spinal therapy apparatus.

Figure 24A:
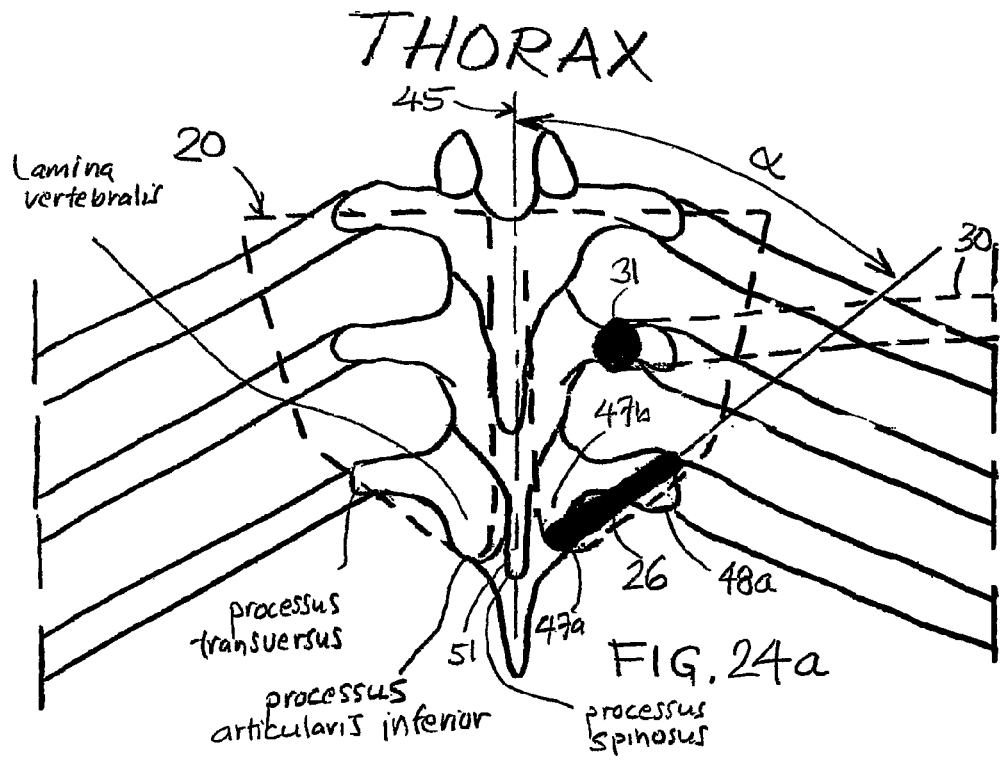

FIG. 24a shows a schematic view of a portion of the thoracic spine of the spinal column 45, the ribs 49 joining with the spinal column 45 and the use of two alternative embodiments of the spinal therapy apparatus according to the invention in this area.

In the first embodiment in FIG. 24a, use is made of a gripping member unit 20 of the spinal therapy apparatus 10, indicated by broken lines, wherein there is only one gripping member 26. The situation shown in FIG. 24a may, exceptionally, also occur when the gripping member unit 20 has two gripping members 26, on either side of the midline of the spinal-column. Such a situation will arise, for example, when the height of the gripping members is adjustable and one of the gripping members 26 has for some reason been adjusted to be higher than the other. In such a case, only the gripping member 26 on one side, that has been adjusted higher, will touch the spinal vertebra as shown in FIG. 24a.

In FIG. 24a, a ridge 26 at the edge of a gripping member in a gripping member unit 20 is placed in FIG. 24a on the right side of the midline 45 of the spinal column, at a vertebra 46, so that the ridge 26 of the gripping member shown by a thick black line applies pressure to both the lamina 47b of the vertebra 46, i.e. the posterior portion of the vertebral arch, i.e. to the processus articularis inferior 47a and the processus transversus 48a of the same vertebra 46, i.e. the transverse process. The angle α between the ridge 26 of the gripping member and the midline of the spinal column is less than 90°.

Ridge 26 of the gripping member does not apply pressure to the processus spinosus, i.e. the spinous process in the central portion of the spinal column 45. When one vertebral interspace in the spinal column 45 in FIG. 24a has been treated, the ridge 26 of the gripping member of the gripping member unit 20 is applied to the next interspace. In this way, the entire spinal column 45 can be treated stage by stage, one vertebral interspace at a time.

In another embodiment of FIG. 24a, the gripping head 31 is used with the help of a shaft portion 30.

Figure 25A:
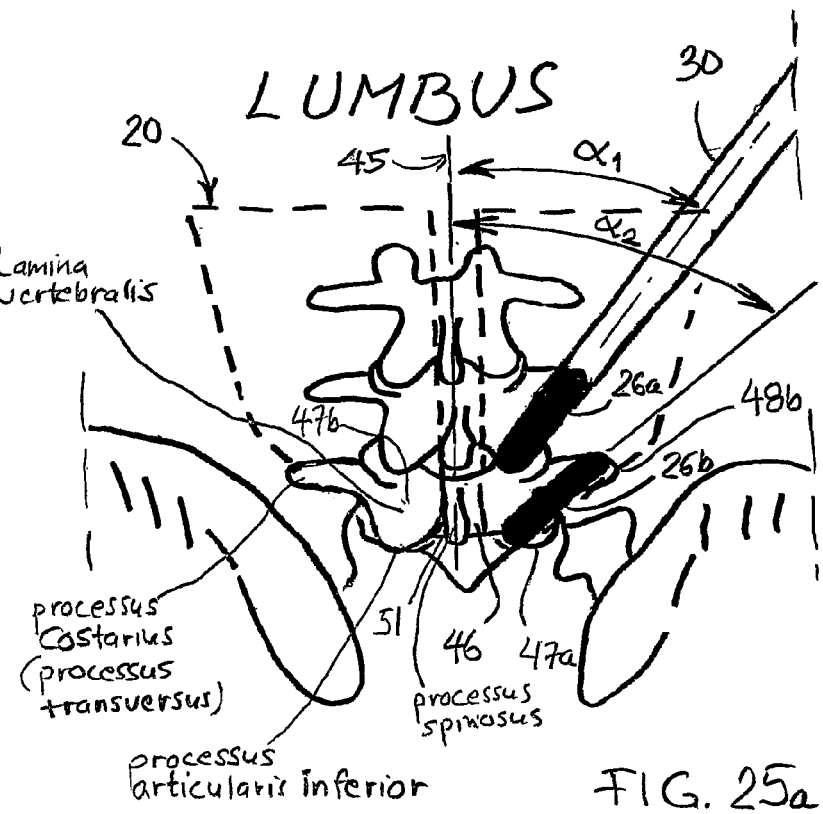

FIG. 25a shows a schematic view of a portion of the lumbar spine in an inferior area of the spinal column 45 and also the use of two alternative embodiments of a spinal therapy apparatus 10 according to the invention.

In the first embodiment in FIG. 25a, the ridge 26b of a gripping member in the form of a wedge located at the edge of a gripping member unit 20 and shown by a thick black line is placed between the lowest vertebra 48 of the spinal column 45 and the iliac bones 50. In such a case, the edge of the ridge 26b of the gripping member applies pressure in the same way both to the lamina 47b or the processus articularis inferior 47a of the vertebra 46 and the costal process 48b, i.e. the processus costarius, of the same vertebra 46. The angle $\alpha_2$ between the ridge 26b of the gripping member and the midline of the spinal column is less than 90°. When one vertebral interspace has been treated, the ridge 26b of the gripping member of the gripping member unit 20 is applied to the next vertebral interspace.

In another embodiment of FIG. 25a, the gripping member 26b is used with the help of a shaft portion 30. The angle $\alpha_1$ between the ridge 26b of the gripping member and the midline of the spinal column is also less than 90°. A similar situation seen from another direction is shown, for example, in FIG. 26, which depicts a gripping member unit 60 equipped with a shaft 30. The curved portion of the shaft portion 30 can be used as a lever when pressing the gripping member 26a against a spinal vertebra.

Figure 24B:
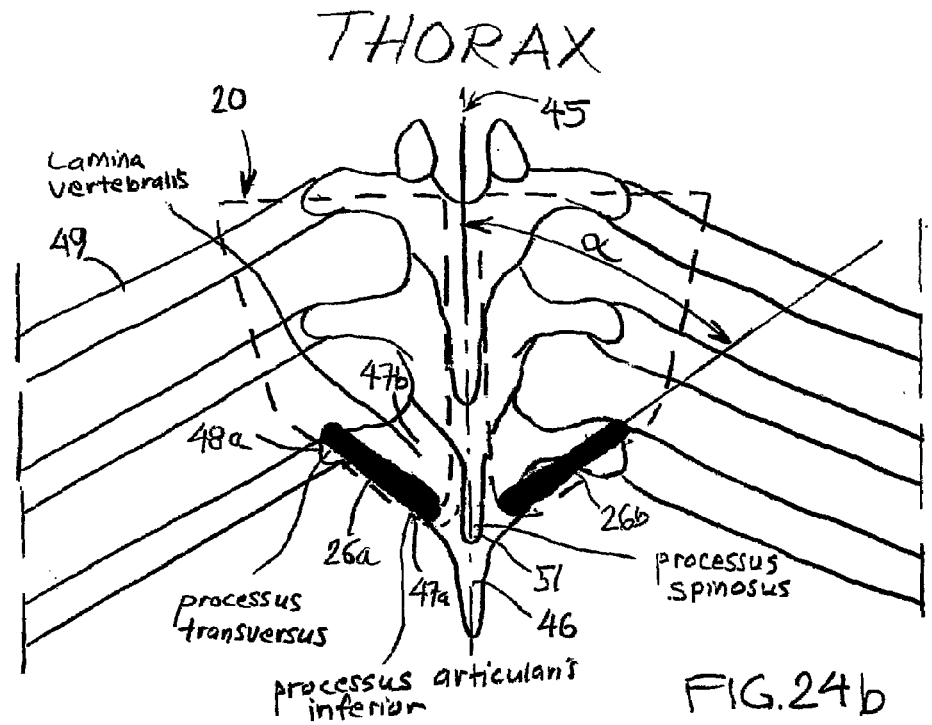

Similarly to FIG. 24a, FIG. 24b also shows a schematic view of a portion of the thoracic spine of the spinal column 45 and the ribs 49 that join with the spinal column 45. However, FIG. 24b shows an embodiment of a spinal therapy apparatus according to the invention in which at the edge of a gripping member unit, there are wedge-shaped ridges 26 of a gripping member, on both sides of the midline of the spinal column 45. The ridges 26 are positioned at a vertebra 46 in the spinal column 45 so that edges of the ridges 26a and 26b of the gripping members depicted with thick black lines apply pressure from both sides of the midline of the spinal column 45 both to the lamina 47b, i.e. the posterior portion of the vertebral arch, of the vertebra 46, or the process processus articularis inferior 47a and the processus transversus 48a, i.e. the transverse process, of the same vertebra 46. The processi spinosi 51, i.e. spinous processes, of the central portion of the spinal column 45 remain between the ridges 26 of the gripping members of the gripping member unit 20 which form a V angle. The angle $\alpha$ between the ridge 26a and the midline of the spinal column is less than 90°. Similarly, the angle $\alpha$ between the ridge 26b and the midline of the spinal column is less than 90°. Consequently, the sum of these angles, i.e. the angle $2\alpha$ between both ridges 26a and 26b is also less than 180°.

When one vertebral interspace in the spinal column 45 has been treated, the ridges 26a and 26b of the gripping members of the gripping member unit 20 are applied to the next vertebral interspace. In this way, the entire spinal column 45 can be treated stage by stage, one vertebral interspace at a time.

Figure 25B:
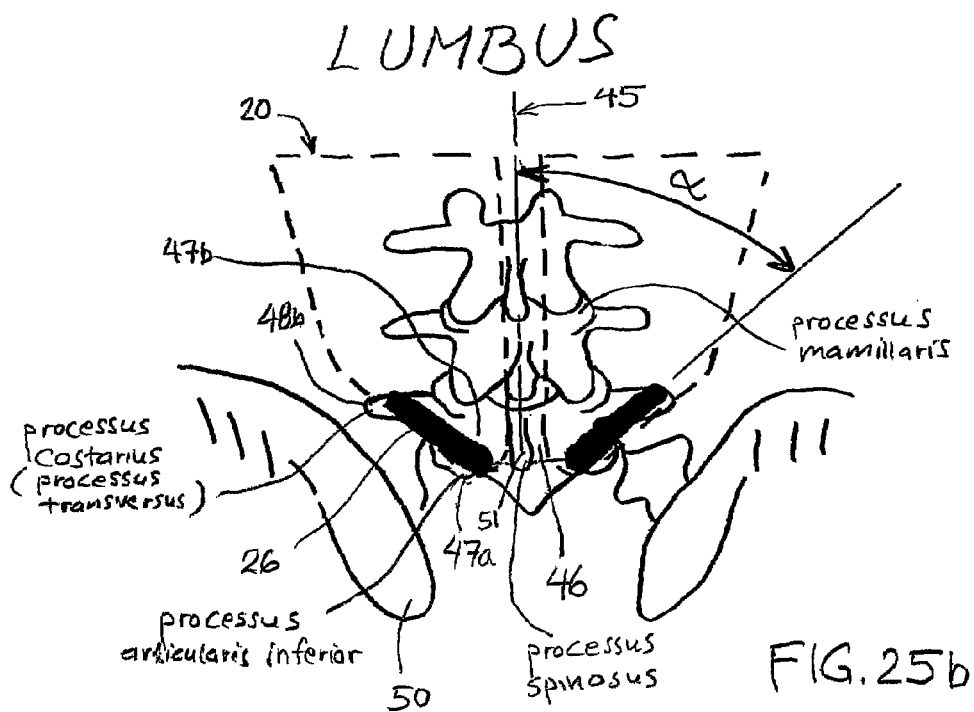

FIG. 25b shows a schematic view of a portion of the lumbar spine in the inferior area of the spinal column 45, as in FIG. 25a. However, there are now two wedge-shaped ridges 26a and 26b of gripping members at the edge of a gripping member unit 20, shown by a thick black line, which are in this case disposed on both sides of the midline of the spinal column 45, between the lowest vertebra 46 and the iliac bones 50. In such a case, the edges of the ridges 26 of the gripping members apply pressure in the same way to both sides of the midline of the spinal column 45, both to the lamina 47b or the processus articularis inferior 47a of the vertebra 46 and the costal process 48b, i.e. processus costarius, of the same vertebra 46. When one vertebral interspace has been treated, the ridges 26a and 26b of the gripping members of the gripping member unit 20 are applied to the next vertebral interspace.

FIGS. 24 and 25 clearly show the benefits of ridges 26a and 26b of the gripping members, which have the form of a V-shaped wedge, of a gripping member unit 20, as the ridges 26a and 26b of the gripping members are always applied only to the structures of a single vertebra 46 at a time, regardless of the height at which the spinal column is located. At the same time, the length of the contact surface makes the use more pleasant. As required, the user can adjust the force and pressure to increase towards the heads by adopting a more up-right position or hang angle. This also increases the traction force.

Figure 26:
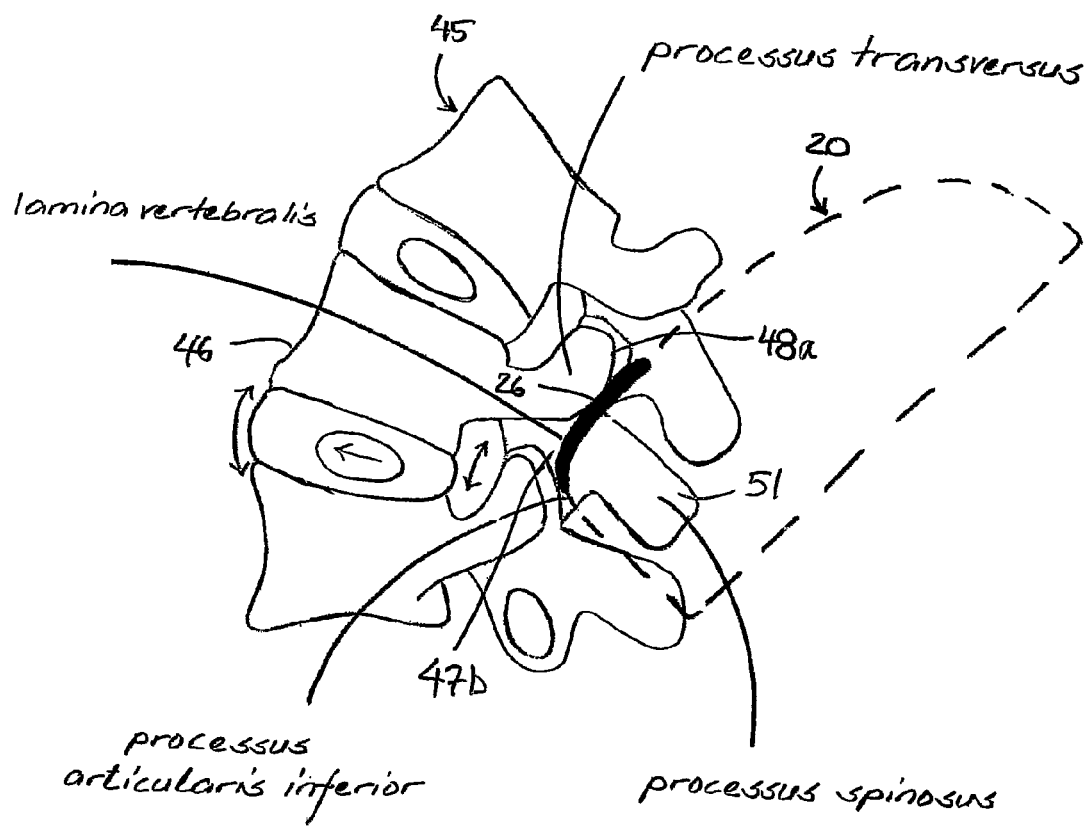

Similarly, FIG. 26 shows a side view of a portion of the spinal column 45 and a gripping member unit 20 of the spinal therapy apparatus, shown by broken lines. A ridge 26 of a gripping member at the edge of the gripping member unit 20, shown by a thick line, applies pressure to the lamina 47b of a vertebra 46 of the spinal column 45, or the processus articularis inferior, and the transverse process 48a, i.e. processus transversus, or the processus costarius, of the same vertebra 46.

Figure 27:
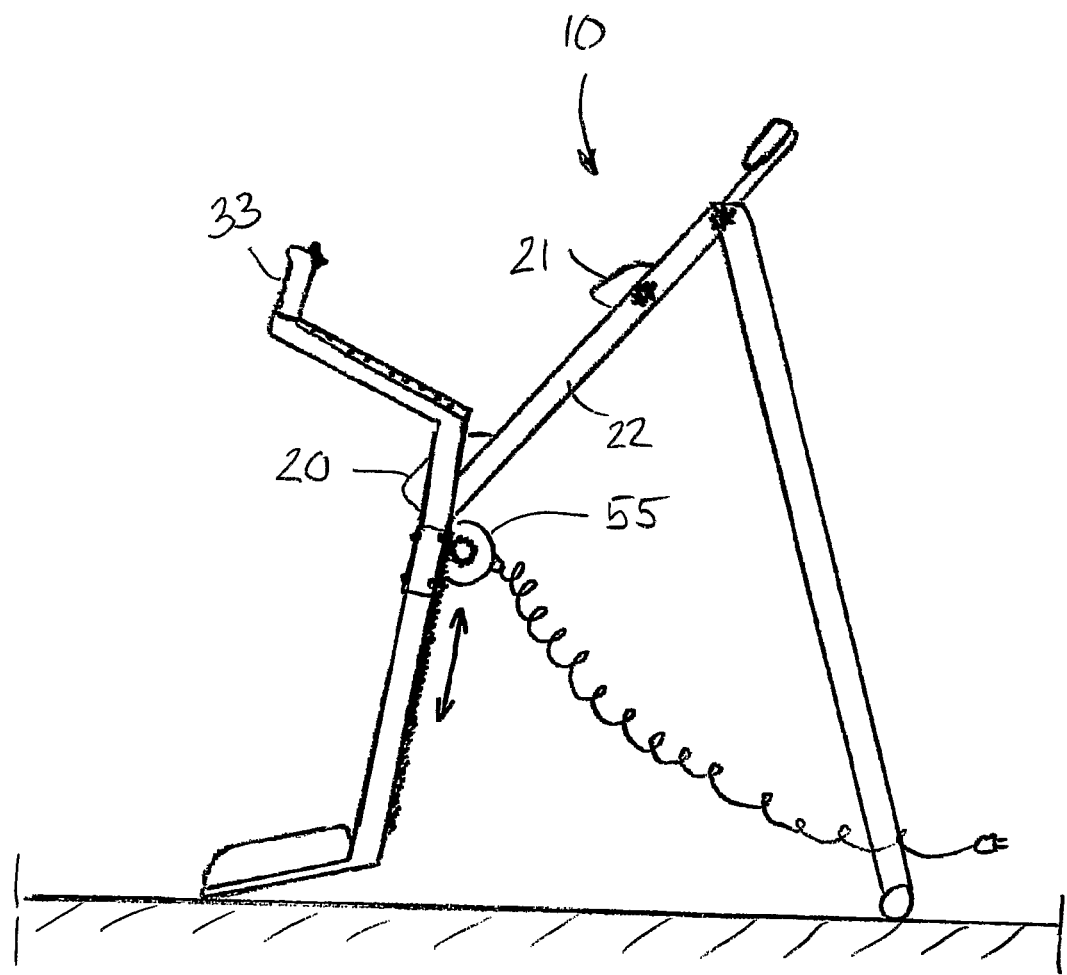
Figure 28:
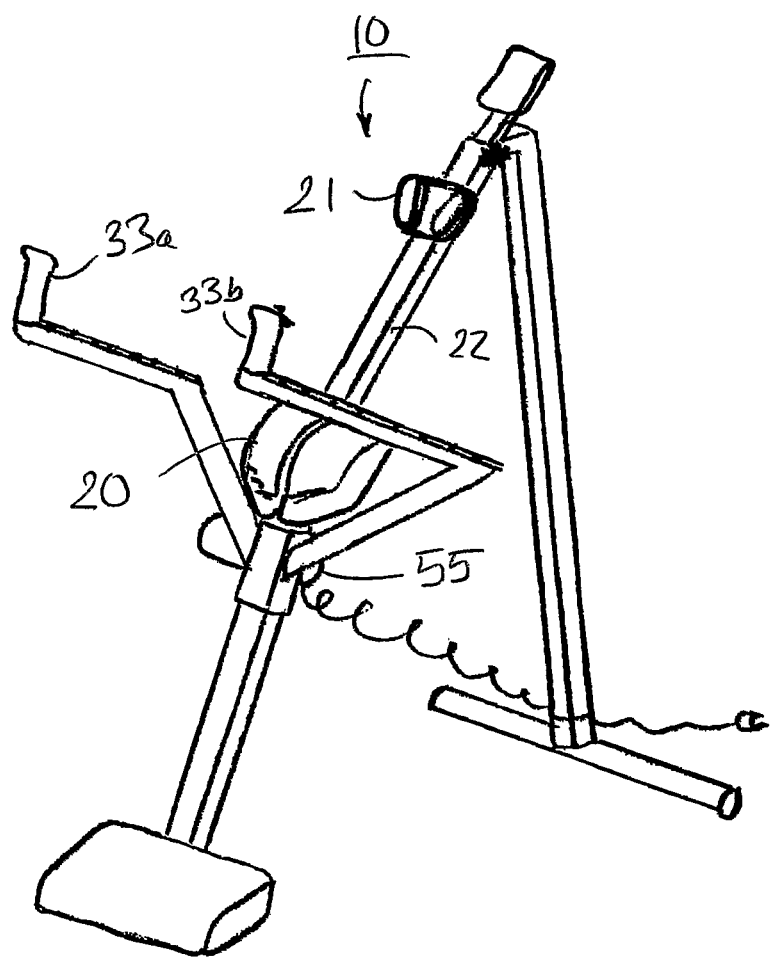

FIG. 27 shows a spinal therapy apparatus 10 with a mechanically controlled device for height adjustment 55. The device can be powered by an electric motor, for example. FIG. 28 shows a perspective view of the apparatus 10 in FIG. 27.

Figure 29:
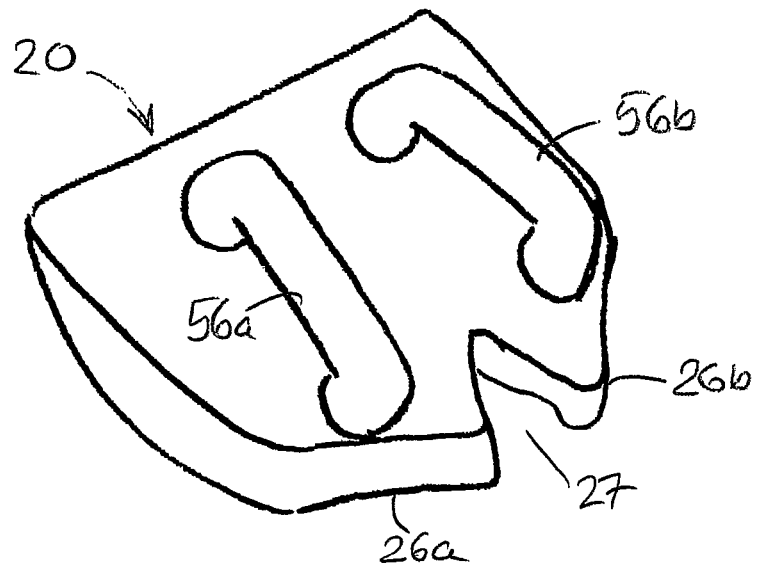

FIG. 29 shows a gripping member unit 20 arranged as a hand-held pressing device. In such a case, a therapist, for example, can treat the spinal vertebrae of a person lying prone from above. In FIG. 29, the ridges of the gripping members are on the opposite side of the pressing pad, and the figure only shows the handles 56a and 56b.

Figure 30:
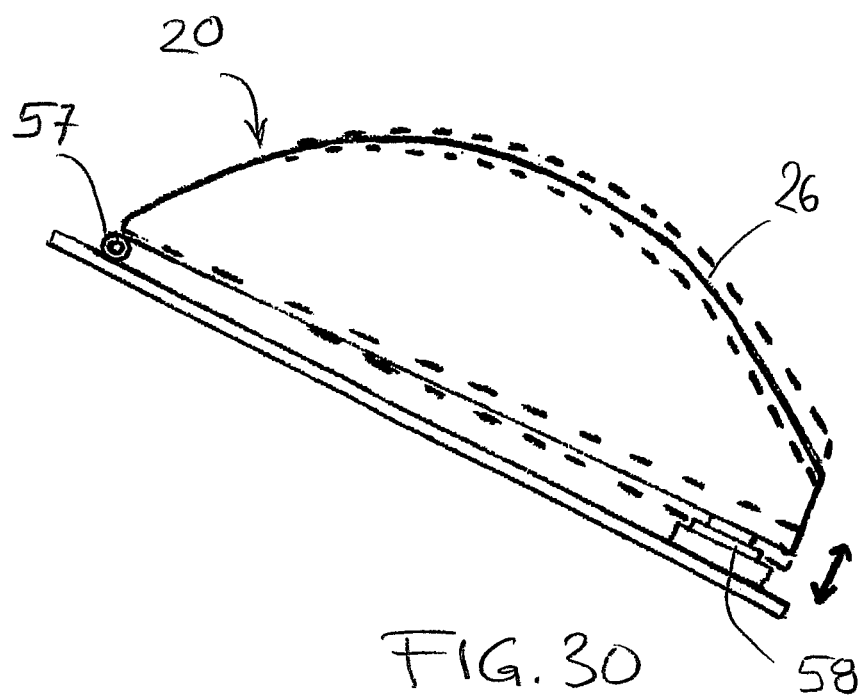

FIG. 30 shows a solution for adjusting the height of a gripping member 26. In this solution, the gripping member 26 is articulated to a height-adjustment joint 57 at its one end and has a height adjustment device 58 at its opposite end.

Figure 31:
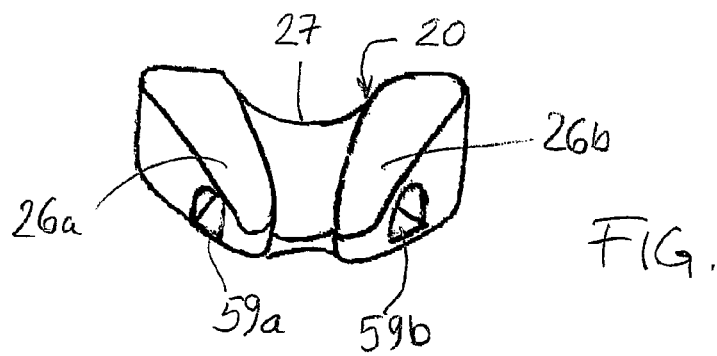
Figure 32:
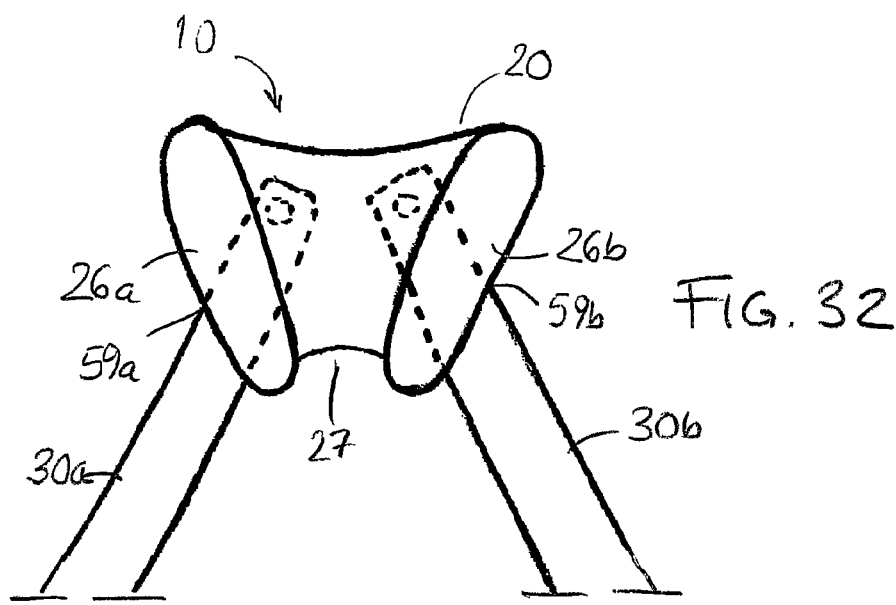
Figure 33:
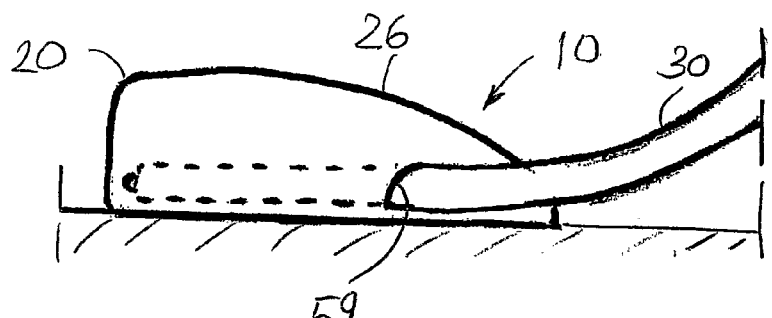

FIG. 31 shows a gripping member unit 20 with two gripping members 26 and with two openings 59a and 59b for detachable shafts. In FIG. 32, shafts 30a and 30b are inserted into the openings 59a and 59b, thus providing a spinal therapy apparatus 10 with shafts. FIG. 33 shows a side view of the spinal therapy apparatus 10 in FIG. 32.

Figure 34:
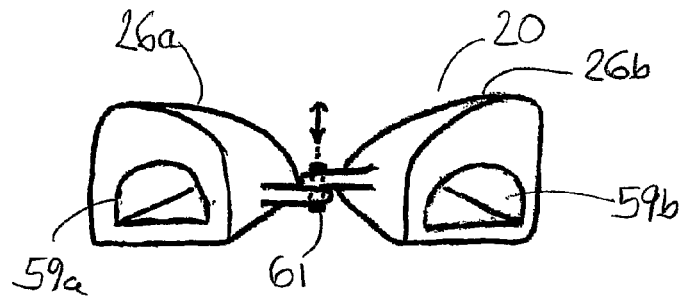
Figure 35:
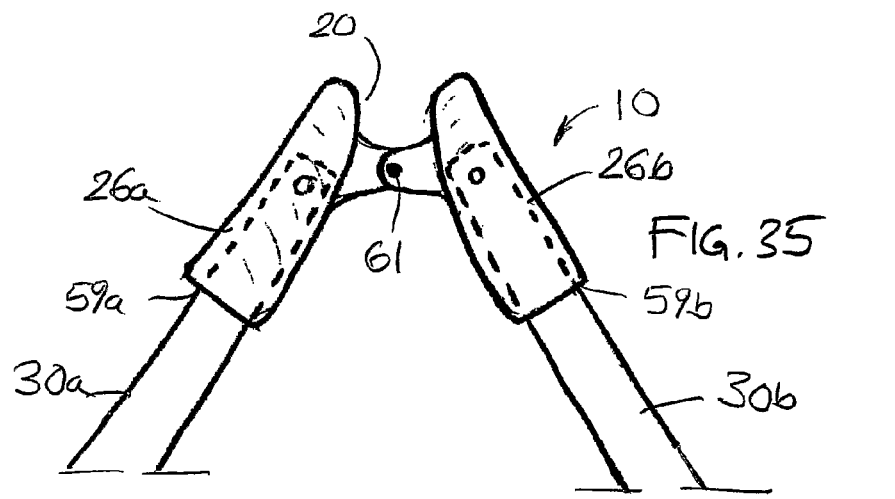

FIG. 34 shows a gripping member unit 20, also with two openings 59a and 59b for detachable shafts, as in FIG. 31. The difference, however, is that the gripping member unit 20 consists of two parts. Both of its halves are attached to each other by means of a detachable hinge pin 61. FIG. 35 shows that, when shafts 30a and 30b are attached to the gripping member unit 20, its gripping members 26a and 26b can be moved relative to each other and thus provide an efficient spinal therapy apparatus 10.

Figure 36:
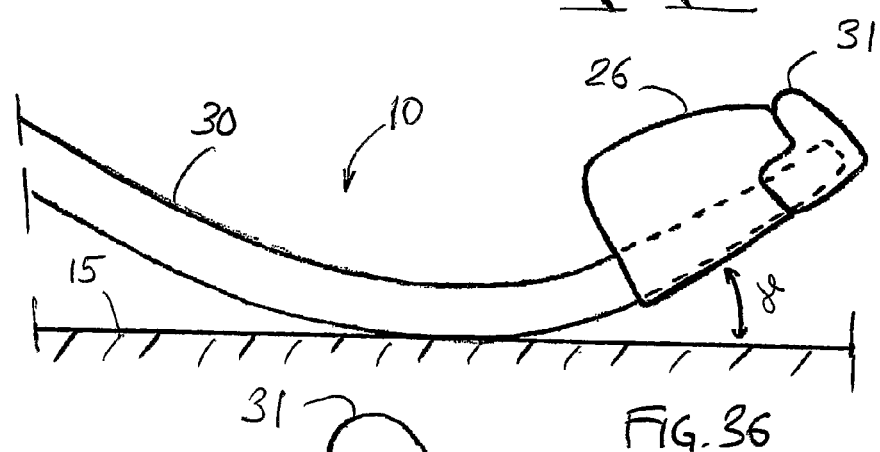
Figure 37:
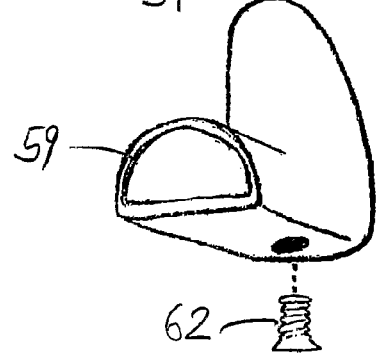

FIG. 36 shows a gripping member 26 with a combined gripping head 31 and shaft 30. The gripping head 31 can be fastened, for example, by means of a locking screw 62, as shown in FIG. 37.

Figure 38:
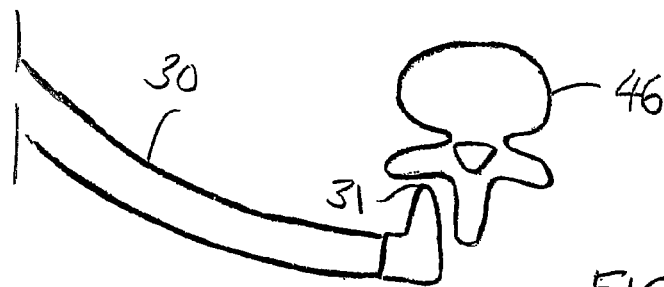

FIG. 38 shows a schematic view of the position of the gripping head 31 at a spinal vertebra 46. The figure shows one method of using the gripping head 31.

Figure 39:
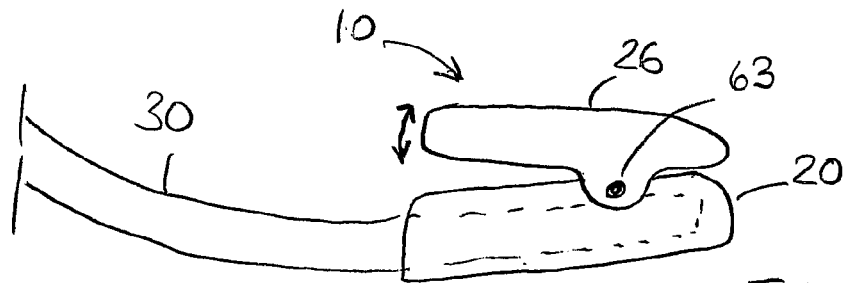
Figure 40:
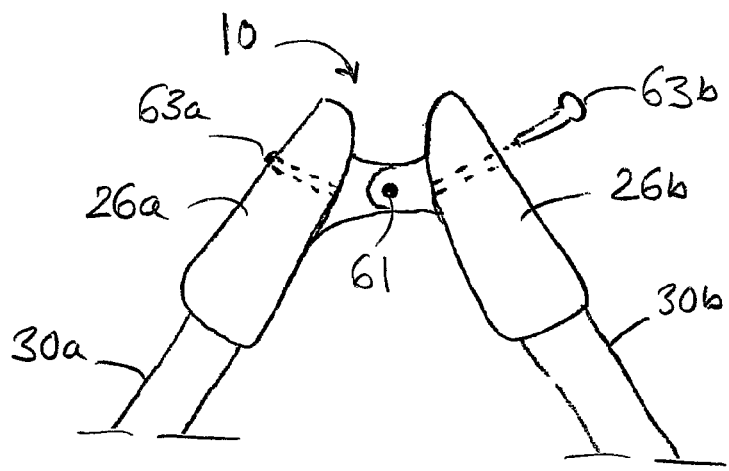

FIG. 39 shows a combination of a shaft 30 and a gripping member unit 20, providing a spinal therapy apparatus 10 equipped with a shaft. FIG. 40 shows a top view of the apparatus. As the figure shows, rocker joint taps 63a and 63b of gripping members 26a and 26b are detachable, as is the hinge pin 61.

Figure 41:
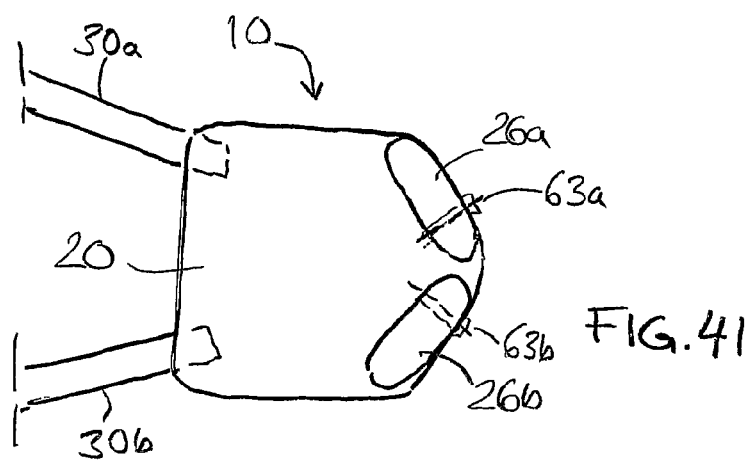

FIG. 41 shows yet another spinal therapy apparatus 10 equipped with shafts 30a and 30b, wherein the gripping member unit 20 consists of a single component.

Figure 42:
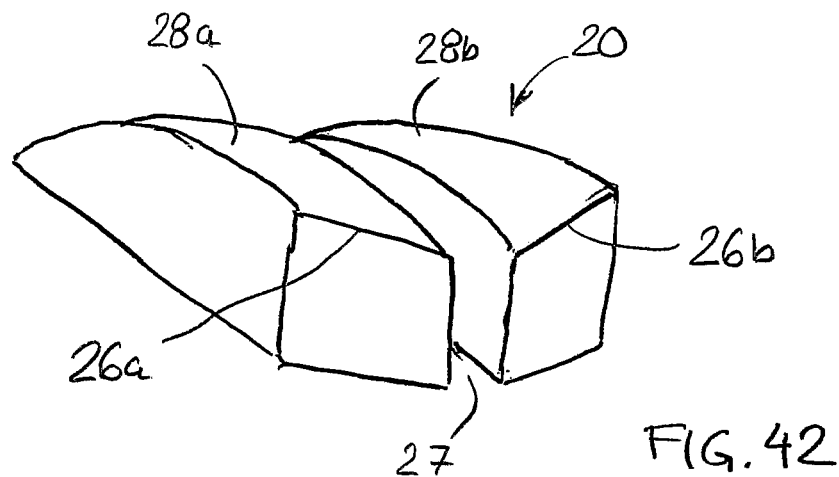

FIG. 42 shows a simplified gripping member unit 20 consisting of two components disposed at a distance from each other, thus having a gap 27 between them. In both of these components, gripping members and their support parts have been combined in a simple fashion, so that the edges of the front portion of the components form the gripping members 26a and 26b. Similarly, the top portions of the components form the support parts 28a and 28b.

Figure 43:
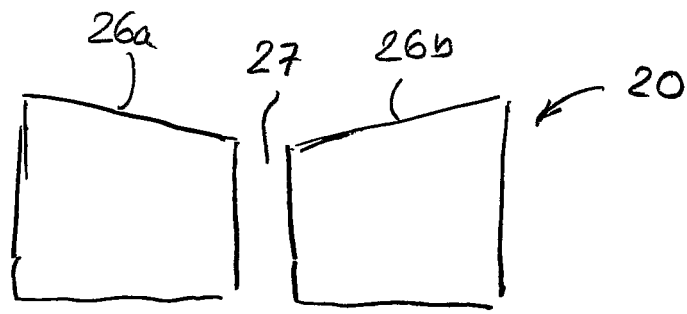

Both FIG. 42 and FIG. 43 giving a front view clearly show that the edges 26a and 26b that comprise the gripping members of the gripping member unit 20 become lower towards the gap between the components.

Figure 44:
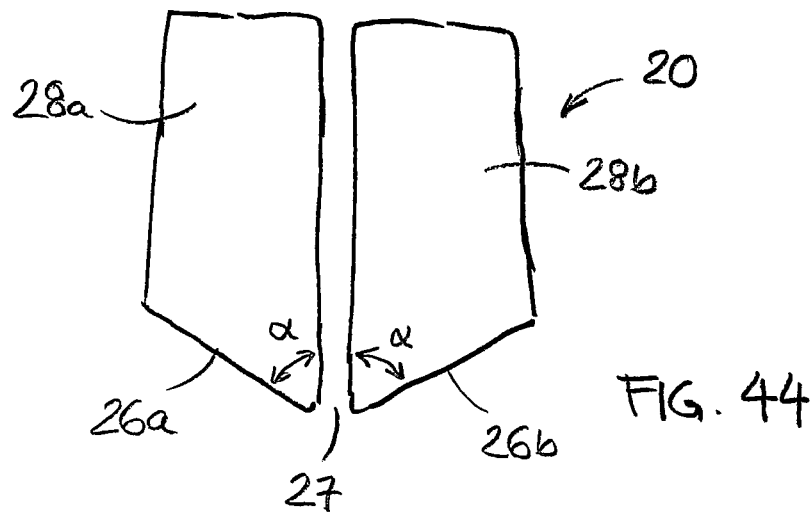

FIG. 44 also shows that the gripping members 26a and 26b form an angle α of less than 90° with the midline. Consequently, the angle 2α between the gripping members 26a and 26b is less than 180°.

FIGS. 45-50 show further embodiments of the gripping member unit 20.

Figure 45:
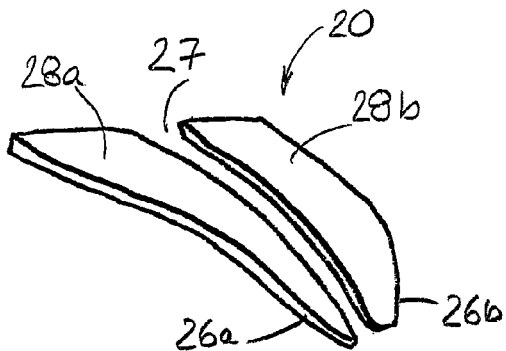
Figure 46:
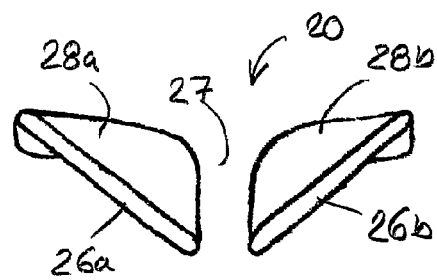

In FIGS. 45 and 46, both halves of the gripping member unit 20 are comprised of plates, the front edges of the plates forming gripping members 26a and 26b and the top surfaces of the plates forming support parts 28a and 28b.

Figure 47:
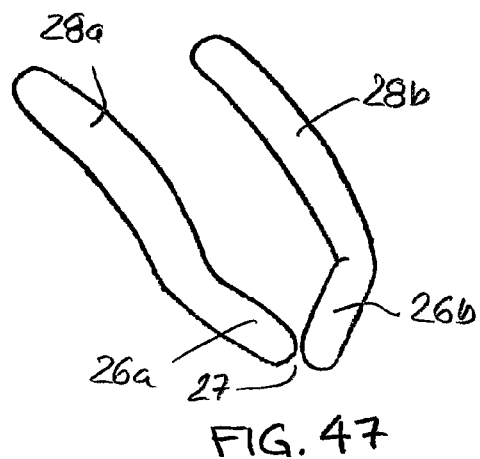
Figure 48:
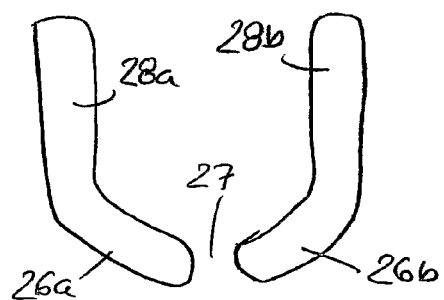

In FIGS. 47 and 48, both halves of the gripping member unit 20 are comprised of round rods so that the front ends of the rods form gripping members 26a and 26b and the opposite ends of the rods form support parts 28a and 28b.

Figure 49:
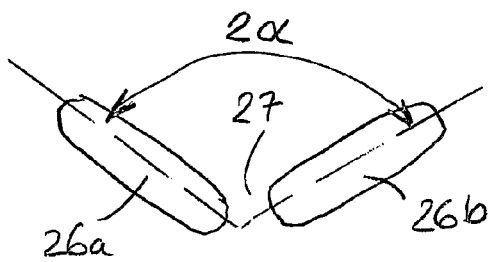

FIG. 49 shows yet another, simpler embodiment wherein the gripping member unit 20 consists only of gripping members 26a and 26b formed by two, round rods located at a distance 27 from each other. The rods are disposed in such a way that the angle 2α between them is less than 180°.

Figure 50:
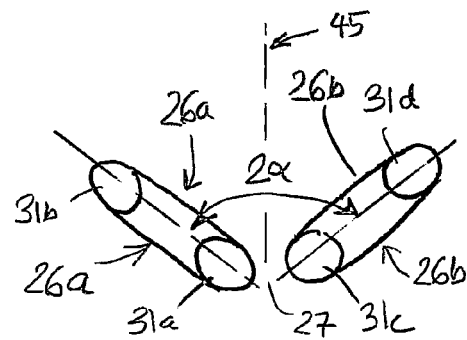

FIG. 50 shows a gripping member unit 20 wherein the first gripping member 26a is formed by two protrusions 31a and 31b. Similarly, another gripping member 26b is formed by two protrusions 31c and 31d. The protrusions 31a and 31b and similarly the protrusions 31c and 31d form two lines of protrusions with the angle 2α between them being less than 180°. There are depressions between the protrusions 31a and 31b and similarly between the protrusions 31c and 31d, which depressions do not in this embodiment substantially rest on the vertebra.

The gripping member unit of FIG. 50 functions in such a way that the protrusions 41a of the gripping member 26a and the corresponding protrusion 31c of the gripping member 26b on the opposite side of the midline 45 rest on the processus articularis inferior of a spinal vertebra or on the inferior portion of a lamina on both sides of the spinal column. Similarly, the protrusion 31b and the protrusion 31d on the opposite side of the midline 45 rest on the processus transversus or the processus costarius of a spinal vertebra, as shown in FIGS. 24b and 25b.

Figure 51:
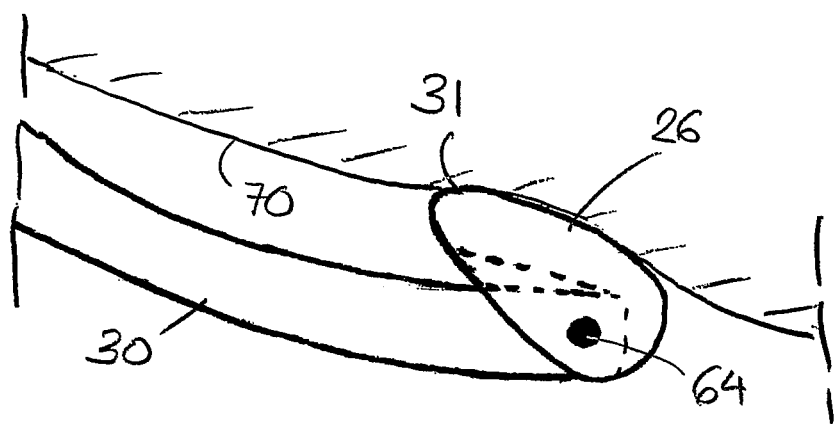

FIG. 51 shows a gripping member 26 equipped with a shaft 30 when pressed against the back of a person 70 using the spinal therapy apparatus. A similar situation is shown in FIG. 25a, where a gripping member 26a equipped with a shaft 30 is shown from another direction.

Figure 52:
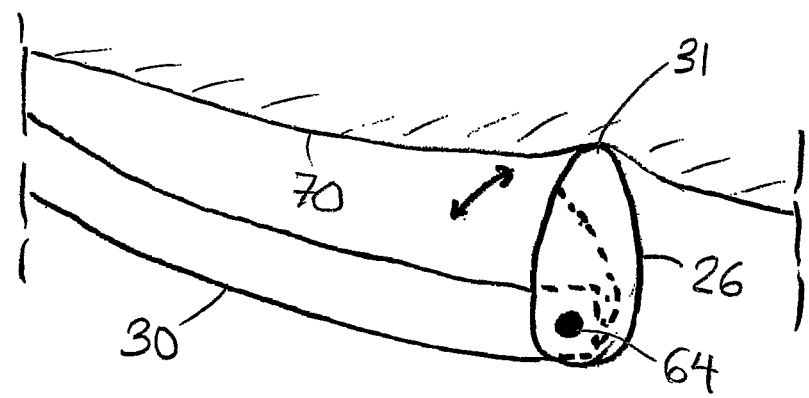

FIG. 52 shows another method of using the gripping member 26 equipped with a shaft 30 in FIG. 51. In this method, the gripping member portion 26 is turned toward the shaft so that a gripping head 31 located on the end of the gripping member 26 is placed against the back of a person 70 using the spinal therapy apparatus. A similar situation is shown in FIG. 24a, where a gripping head 31 equipped with a shaft 30 is shown from another direction.

Additional Notes

It is obvious to a person skilled in the art that the different embodiments of the invention may vary within the scope of the claims presented below.

LIST OF REFERENCE NUMBERS 10 spinal therapy apparatus
11 chair
12 support rack
13 linking rod
14 additional weight
15 floor
16 wall
17 door
18 mat
19 ceiling
20 gripping member unit—(lower pad)
21 gripping member unit—(upper pad)
22 linking frame
23 floor rest
24 fastening strap
25 padding
26 gripping member (ridge)
27 groove or gap between gripping members
28 support part
29 hinge of a gripping member unit
30 shaft (handle)
31 gripping head (hook for treating vertebrae)
32 additional support
33 handle
34 additional handle
35 hook
36 hinge
37 wedge
38 space
39 groove
40 rope handle
41 seat
42 replaceable head
43 frictional bushing
44 connecting strap
45 midline of the spinal column
46 vertebra
47a processus articularis inferior
47b inferior portion of the lamina (inferior portion of the lamina vertebralis, inferior portion of the vertebral arch)
48a processus transversus (transverse process in the thoracic spine)
48b processus costarius (costal process in the lumbar spine)
49 rib (costa)
50 iliac bone (ilium)
51 processus spinosus
52 ball 53 string
54 rubber band
55 height adjustment device of a gripping member unit
56 handle
57 height adjustment joint of a gripping member unit
58 height adjustment device of a gripping member
59 opening
61 hinge pin
62 locking screw
63 rocker joint tap of a gripping member
64 groove for a skin fold
70 user of the apparatus, person
α angle between the gripping member unit and the midline of the spinal column
β reclining angle
γ angle of the shaft relative to the base

The invention claimed is:

1. A spinal therapy apparatus including at least one member to be placed against the back of a user of said apparatus for treating vertebrae in a spinal column, characterised in that
said at least one member is a gripping member unit comprising a groove extending in a longitudinal direction of the gripping member unit and two elongated gripping members on opposite sides of said groove,
each of said elongated gripping members having a longitudinal axis forming an oblique angle with respect to the longitudinal direction of the gripping member unit and comprising a longitudinal ridge, a longitudinal rounded edge, or a longitudinal line formed by two or more protrusions which can be directed to apply pressure to selected vertebra, and said gripping member unit is movable in said spinal therapy apparatus so as to place said elongated gripping members between the spinal vertebrae of the user of said apparatus, a single vertebra or a vertebral interspace at a time,
when said spinal therapy apparatus is placed against the back of a user, one end of the longitudinal ridge, longitudinal rounded edge, or longitudinal line of each of said elongated gripping members is close to the spinal column, at a distance from it, and the opposite end of the longitudinal ridge, longitudinal rounded edge, or longitudinal line of each of said elongated gripping members is directed away from the spinal column, diagonally sideways, diverging from the transverse direction of the spinal column and partly towards the shoulder of the user and an angle α is formed between the longitudinal axis of each of said elongated gripping members and the longitudinal direction of the gripping member unit and is less than 90°; and further characterised in that
said spinal therapy apparatus includes at least one support handle which the user of said spinal therapy apparatus can hold, support himself or herself on, lean against, or hang on in order to move the selected vertebra to the elongated gripping members of said gripping member unit.

2. The spinal therapy apparatus as claimed in claim 1, wherein the angle α formed between the longitudinal axis of each of said elongated gripping members and the longitudinal direction of the gripping member unit is 15°-80°.

3. The spinal therapy apparatus as claimed in claim 1, further characterised in that said spinal therapy apparatus comprises
a frame (22), and
said gripping member unit further comprises
two support parts on which the user of the spinal therapy apparatus can lean, each of said support parts being arranged in the vicinity of and above each of said elongated gripping members, said support parts being padded or hard, and
a depression or a gap arranged between said support parts and said elongated gripping members.

4. The spinal therapy apparatus as claimed in claim 3, wherein, when said spinal therapy apparatus is arranged on a floor, said gripping member unit is located above the floor at sitting height or at standing height, at least a portion of said gripping member unit being tilted forward and each of said elongated gripping members being at the same level or angled downwardly towards an opposite elongated gripping member and correspondingly angled upwardly towards the outer edge of said gripping member unit, and in that there is a groove or a gap between said elongated gripping members and said support parts of said gripping member unit.

5. The spinal therapy apparatus as claimed in claim 4, wherein an angle of said spinal therapy apparatus or said gripping member unit relative to the floor is 30°-70°.

6. The spinal therapy apparatus as claimed in claim 3, characterised in that said support parts are arranged obliquely relative to a floor.

7. The spinal therapy apparatus as claimed in claim 1, further characterised in that said spinal therapy apparatus includes a lower gripping member unit and an upper gripping member unit, and an inclination and distance of the gripping member units relative to each other can be adjusted.

8. The spinal therapy apparatus as claimed in claim 1, wherein said spinal therapy apparatus includes at least one pair of support handles, which at least one pair of support handles are located in front of or behind said gripping member unit, above it, level with said gripping member unit or below said gripping member unit, and each of said support handles is selected from the group consisting of a curved rod directed upwards, a handle directed to the side or forward, a rope handle and an armrest.

9. The spinal therapy apparatus as claimed in claim 1, further characterised in that
said at least one support handle includes a shaft portion, said shaft portion being an upwards-directed, padded, curved rod; said shaft portion being attached to a frame of said spinal therapy apparatus so as to turn around it and said shaft portion having a rounded end portion at the end of its support handle, which end portion forms a gripping head;
said shaft portion being detachable from said frame so that said gripping head can be used separately for applying pressure to or massaging or mobilising the back or for rotation.

10. The spinal therapy apparatus as claimed in claim 9, further characterised in that
said spinal therapy apparatus includes a floor rest with adjustable length and inclination, which floor rest, when said spinal therapy apparatus is fastened to a supporting member, keeps said spinal therapy apparatus in its place and prevents said supporting member from tilting forward and simultaneously functions as a strap tightener,
and said floor rest is padded such that it provides a backrest when treating a neck.

11. The spinal therapy apparatus as claimed in claim 10, characterised in that said spinal therapy apparatus includes a rubber mat to be fastened to said supporting member, said rubber mat preventing the supporting member from sliding backwards and functioning as a mat for lying on when using said gripping head.

12. A spinal therapy apparatus as claimed in claim 1, further characterised in that said spinal therapy apparatus includes a fastening for fastening said spinal therapy apparatus to a chair, stand, rack or other supporting member to prevent said spinal therapy apparatus from sliding backwards.

13. A spinal therapy apparatus as claimed in claim 1, characterised in that
said spinal therapy apparatus is removably attachable to a chair and includes two supports to be attached to the chair for resting on a floor, which supports can be turned around and tilted to a suitable position according to the height of the chair and which can be detached for transport;
wherein both of said supports are provided with a handle that can be adjusted in the vertical direction.

14. The spinal therapy apparatus as claimed in claim 1, characterised in that said spinal therapy apparatus includes a supporting structure selected from support legs and a support rack.

15. The spinal therapy apparatus as claimed in claim 1, characterised in that the angle $\alpha$ formed between the longitudinal axis of each of said elongated gripping members and the longitudinal direction of the gripping member unit is 40°-60°.

16. The spinal therapy apparatus as claimed in claim 1, wherein an angle of said spinal therapy apparatus or said gripping member unit relative to the floor (15) is 40°-50°.

17. A spinal therapy apparatus including at least one member to be placed against the back of a user of said apparatus for treating vertebrae in a spinal column, characterised in that
said at least one member is a gripping member unit comprising a pad-like member separated into two halves by a groove having a longitudinal axis and extending a length of the gripping member unit, said groove being adapted in size and position such that said halves are arranged on opposite sides of a spine of the user when the spinal therapy apparatus is in use;
each of said halves having a first end and a second end in the direction of said groove, an elongated gripping member formed at the first end of each of said halves and a user support part formed at the second end of each of said halves;
each elongated gripping member comprising a longitudinal ridge, a longitudinal rounded edge, or a longitudinal line formed by two or more protrusions, and having a longitudinal axis that is oblique with respect to the longitudinal axis of said groove, an angle ($\alpha$) of 15°-80° being formed between the longitudinal axis of each of said elongated gripping members and the longitudinal axis of said groove;
said gripping member unit being movable in said spinal therapy apparatus so as to place said elongated gripping members between the spinal vertebrae of the user a single vertebra or a vertebral interspace at a time; and
when said spinal therapy apparatus is in use, the gripping member unit is placed against the back of a user, one end of the longitudinal ridge, longitudinal rounded edge, or longitudinal line of each of said elongated gripping members being close to the spinal column, at a distance from it, and the opposite end of the longitudinal ridge, longitudinal rounded edge, or longitudinal line being directed away from the spinal column, diagonally sideways, diverging from the transverse direction of the spinal column and partly towards the shoulder of the user;
said spinal therapy apparatus being further characterised in that
said spinal therapy apparatus includes at least one support handle which the user of said spinal therapy apparatus can hold, support himself or herself on, lean against, or hang on in order to move the selected vertebra to the elongated gripping members of said gripping member unit.

18. The spinal therapy apparatus of claim 17, wherein the separate halves of the gripping member unit are joined to each other by a hinge pin at said second end such that the distance between the gripping members of the gripping member unit is adjustable.

* * * * *